US008889069B2

(12) United States Patent
Fukuma et al.

(10) Patent No.: US 8,889,069 B2
(45) Date of Patent: Nov. 18, 2014

(54) SAMPLE PROCESSING APPARATUS AND A METHOD OF CONTROLLING A SAMPLE PROCESSING APPARATUS

(71) Applicant: Sysmex Corporation, Kobe (JP)

(72) Inventors: Daigo Fukuma, Kobe (JP); Keisuke Kuwano, Kobe (JP)

(73) Assignee: Sysmex Corporation (JP)

( * ) Notice: Subject to any disclaimer, the term of this patent is extended or adjusted under 35 U.S.C. 154(b) by 67 days.

(21) Appl. No.: 13/627,513

(22) Filed: Sep. 26, 2012

(65) Prior Publication Data

US 2013/0079919 A1    Mar. 28, 2013

(30) Foreign Application Priority Data

Sep. 28, 2011   (JP) ................................. 2011-211828

(51) Int. Cl.
| | |
|---|---|
| G01N 33/00 | (2006.01) |
| G01N 21/00 | (2006.01) |
| G01N 35/02 | (2006.01) |
| G01N 35/00 | (2006.01) |
| G01N 35/10 | (2006.01) |
| G01N 33/48 | (2006.01) |
| G01N 33/49 | (2006.01) |
| G01N 35/04 | (2006.01) |

(52) U.S. Cl.
CPC ............... *G01N 35/00* (2013.01); *G01N 33/49* (2013.01); *G01N 35/026* (2013.01); *G01N 35/00732* (2013.01); *G01N 35/1004* (2013.01); *G01N 2035/0412* (2013.01)
USPC ................. 422/67; 422/68.1; 422/73; 422/64

(58) Field of Classification Search
CPC   G01N 35/026; G01N 35/00663; G01N 35/02
USPC .......................................................... 422/67
See application file for complete search history.

(56) References Cited

U.S. PATENT DOCUMENTS

| | | | | |
|---|---|---|---|---|
| 5,993,739 | A  * | 11/1999 | Lyon ............................... | 422/31 |
| 2007/0116599 | A1* | 5/2007 | Walters et al. ................... | 422/64 |
| 2008/0050279 | A1* | 2/2008 | Fujita .............................. | 422/67 |
| 2010/0104478 | A1* | 4/2010 | Kondou ......................... | 422/100 |
| 2010/0108101 | A1 | 5/2010 | Shibata et al. | |

FOREIGN PATENT DOCUMENTS

JP          2003-254980 A      9/2003

* cited by examiner

*Primary Examiner* — Jill Warden
*Assistant Examiner* — Brittany Fisher
(74) *Attorney, Agent, or Firm* — Brinks Gilson & Lione

(57) ABSTRACT

A sample processing apparatus is disclosed. The apparatus comprises a sample processing section, a transporting section, an identification data acquirer and a system controller. When identification data of a washing fluid tube is acquired by the identification data acquirer, the system controller controls the transporting section to supply the washing fluid tube to the sample processing section. When the washing fluid tube arrives at the sample processing section, the sample processing section aspirates the washing fluid in the supplied washing fluid tube and performs a washing of at least one part of the sample processing section. The system controller prohibits the washing with the washing fluid tube if identification data of a sample tube is acquired after the identification data of the washing fluid tube is acquired and before the washing is started.

19 Claims, 18 Drawing Sheets

DOWNSTREAM ←——→ UPSTREAM

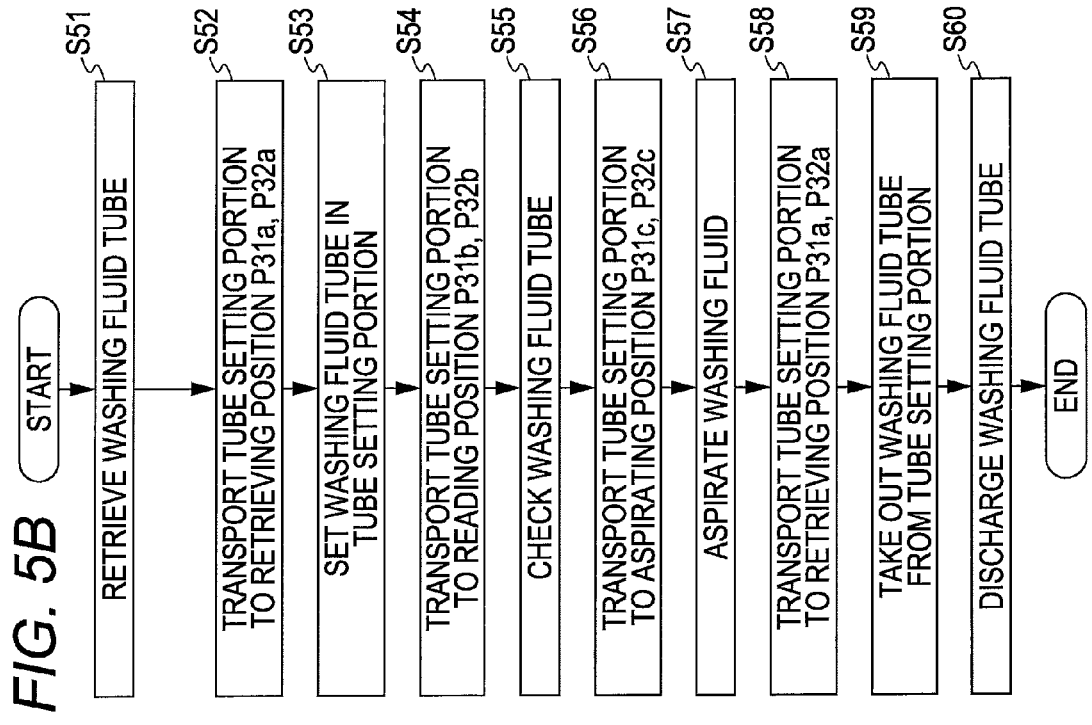
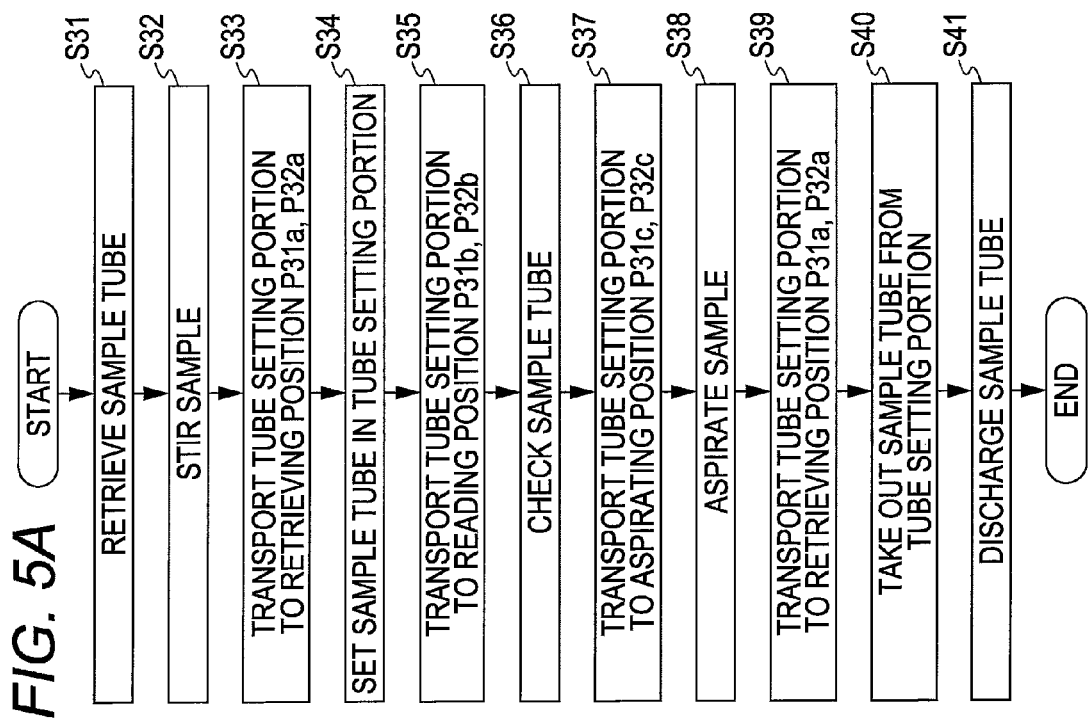

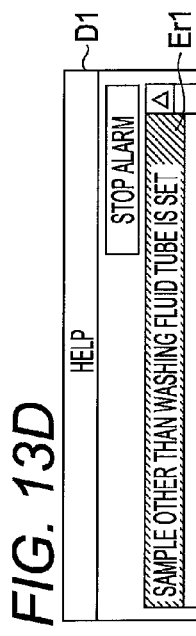
FIG. 13A
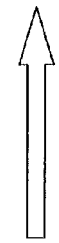
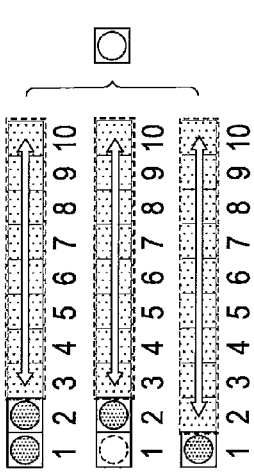
FIG. 13D
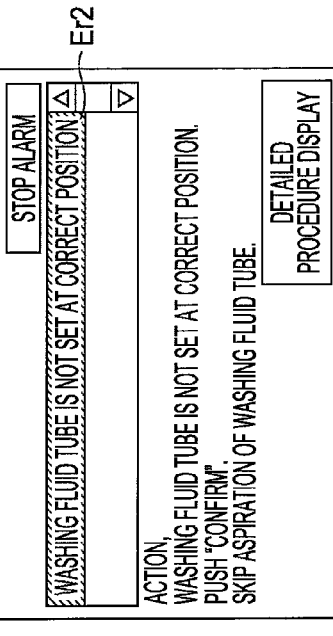
FIG. 13B
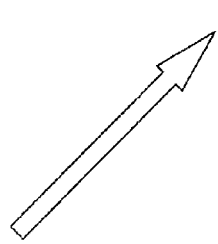
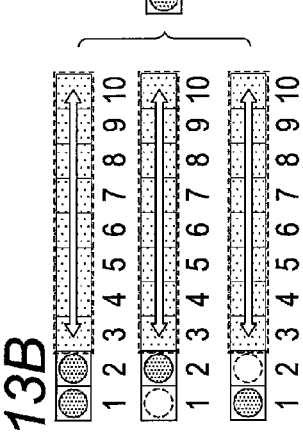
FIG. 13E
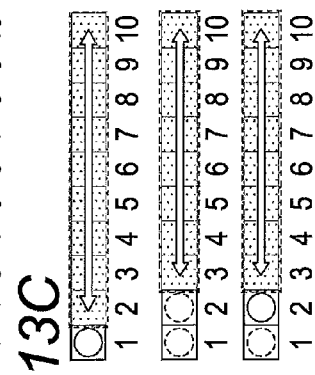
FIG. 13C
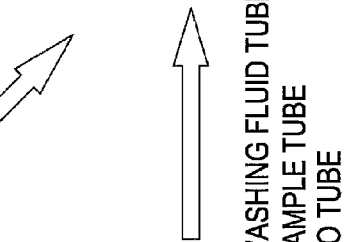

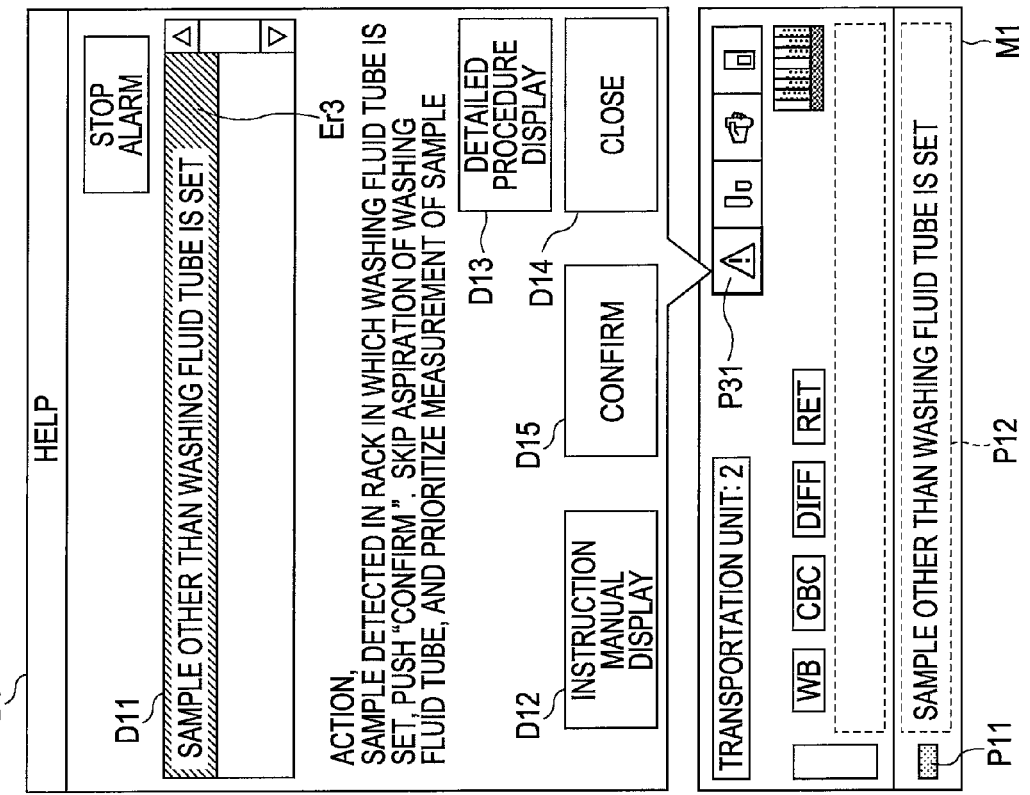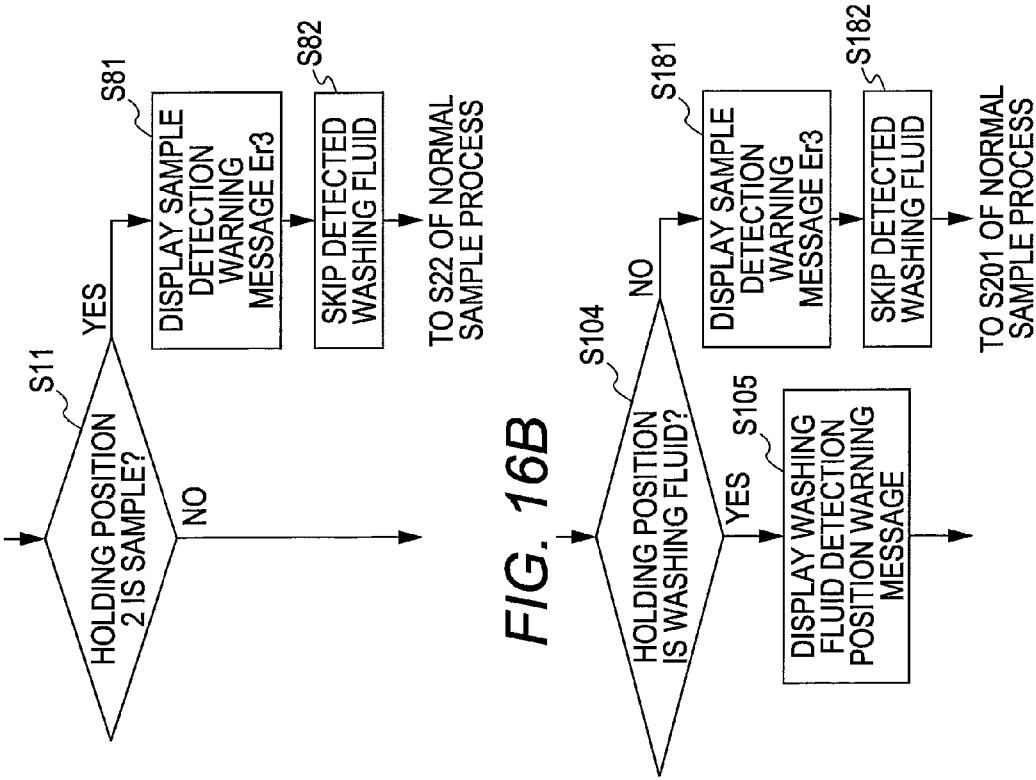

SAMPLE PROCESSING APPARATUS AND A METHOD OF CONTROLLING A SAMPLE PROCESSING APPARATUS

RELATED APPLICATIONS

This application claims priority under 35 U.S.C. §119 to Japanese Patent Application No. 2011-211828 filed on Sep. 28, 2011, the entire content of which is hereby incorporated by reference.

FIELD OF THE INVENTION

The present invention relates to a sample processing apparatus for processing a sample such as blood, urine or the like. The present invention also relates to a method of controlling a sample processing apparatus.

BACKGROUND OF THE INVENTION

A sample processing apparatus for aspirating a sample, such as blood or urine, accommodated in a sample tube by an aspiration tube, and processing the sample is known.

Use of a sample processing apparatus for a long period of time may cause dirt accumulation in the fluid system such as the aspiration tube, flow path, valve, reaction tube, analyzing section, and the like. This may cause a deterioration of accuracy or an operation failure. The fluid system thus needs to be periodically washed after the apparatus completes operation or for every predetermined number of processing samples.

JP Laid-open Patent No. 2003-254980 discloses a specimen analyzer for aspirating washing fluid in a fluid tube with an aspirating section, and performing a washing of interior of fluid circuit. In this configuration, when a rack holding the washing fluid tube is set in the specimen analyzer, the set rack is transported. When the washing fluid tube held in the rack is recognized by the apparatus, the washing fluid is automatically aspirated from the washing fluid tube and the fluid circuit is washed.

The washing of the fluid circuit using the washing fluid includes filling a chamber, a detection unit, and a flow path connecting the same with the washing fluid, leaving it for a certain time to remove the dirt accumulated inside the chamber and the flow path. It takes a long time for performing a washing. Therefore, when performing the automatic washing using the washing fluid, it is preferred that the washing fluid is supplied to the sample processing apparatus after sample tubes are supplied to the sample processing apparatus and samples therein are processed by the sample processing apparatus.

However, if the sample tube and the washing fluid tube are set so that the washing fluid tube is supplied to the sample processing apparatus before the sample tube is supplied to the sample processing apparatus, the automatic washing will be started before the processing of the sample in the sample tube. In such case, the sample to be processed has to wait until the washing is completed.

SUMMARY OF THE INVENTION

A first aspect of the present invention is a sample processing apparatus for processing a sample, the sample processing apparatus comprising: a sample processing section configured to aspirate a sample in a sample tube and process the aspirated sample; a transporting section configured to transport a plurality of tubes so that the sample processing section is sequentially supplied with the tubes; an identification data acquirer configured to acquire identification data of the tube being transported towards the sample processing section; and a system controller configured to: control the transporting section, when identification data of a washing fluid tube is acquired, to supply the washing fluid tube to the sample processing section; control the sample processing section, when the washing fluid tube arrives at the sample processing section, to aspirate the washing fluid in the supplied washing fluid tube and to perform a washing of at least one part of the sample processing section, wherein the system controller prohibits the washing with the washing fluid tube if identification data of a sample tube is acquired after the identification data of the washing fluid tube is acquired and before the washing is started.

A second aspect of the present invention is a sample processing apparatus for processing a sample comprising: a sample processing section configured to aspirate and perform a process on a sample in a sample tube; a transporting section configured to transport a plurality of tubes so that the sample processing section is sequentially supplied with the tubes; an identification data acquirer configured to acquire identification data of a tube being transported towards the sample processing section; and a system controller, wherein the system controller prohibits a supply of a washing fluid tube to the sample processing section when recognizing based on the identification data that the washing fluid tube is followed by a sample tube; and the system controller controls the sample processing section to aspirate the washing fluid in the washing fluid tube and use it to wash a part of the sample processing section when any presence of a sample tube following the washing fluid tube is not recognized.

A third aspect of the present invention is a method of controlling a sample processing apparatus comprising the steps of: (a) transporting a tube to a first position; (b) acquiring identification data from the tube at the first position to determine whether the tube is a sample tube or a washing fluid tube; (c) transporting the tube to a second position for supplying the tube to a sample processing section if the tube is determined as a sample tube in the determination of (b); (d) executing a processing on a sample in the sample tube by the sample processing section when the sample tube arrives at the second position; (e) transporting the tube to the second position for supplying the tube to the sample processing section if the tube is determined as a washing fluid tube in the determination of (b); (f) executing a washing with a washing fluid in the washing fluid tube by the sample processing section when the washing fluid tube arrives at the second position; and (g) cancelling the step (f) when identification data is acquired from a tube at the first position and determination is made that the tube is a sample tube before the step (f) is started.

BRIEF DESCRIPTION OF THE DRAWINGS

FIG. 5A is a view showing a flowchart of retrieving operation of the sample tube of the measurement unit according to the embodiment;

FIG. 5B is a view showing a flowchart of retrieving operation of the washing fluid tube of the measurement unit according to the embodiment;

FIG. 13A-13E are views showing relationships of the warning message outputs and tube arrangement examples according to the embodiment;

FIGS. 16A and 16B are views showing flowcharts of operation of rack according to modified embodiment 2;

FIG. 16C is a view showing a warning message according to modified embodiment 2

DETAILED DESCRIPTION OF THE PREFERRED EMBODIMENTS

The sample processing apparatus according to the present embodiment will be hereinafter described with reference to the drawings.

Figure 1:
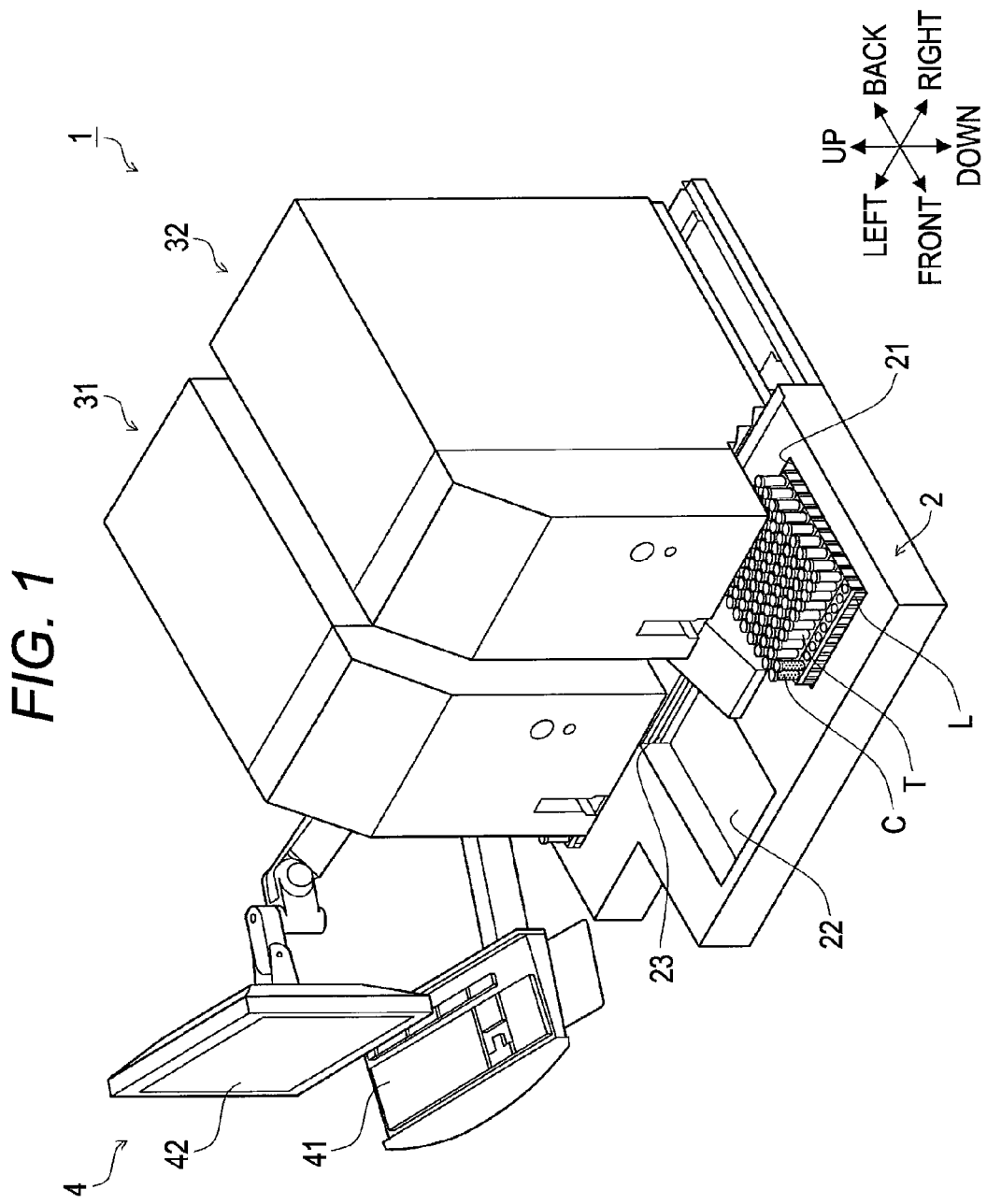
FIG. 1 is a perspective view showing an outer appearance of a sample analyzer according to an embodiment.

FIG. 1 is a perspective view showing an outer appearance of a sample processing apparatus 1. The sample processing apparatus 1 according to the present embodiment is configured by a transportation unit 2, measurement units 31, 32, and an information processing unit 4 (system controller). The measurement units 31, 32 are blood cell counters.

The transportation unit 2 is arranged on a front side of the measurement units 31, 32, and includes a right table 21, a left table 22, and a rack transporting portion 23 for connecting the right table 21 and the left table 22. The right table 21 and the left table 22 are able to accommodate a plurality of racks L capable of holding at most the tubes, where the tube means sample tube T or washing fluid tube C.

The transportation unit 2 is configured to receive a rack L from a user and to accommodate the rack L on the right table 21. The transportation unit 2 transports the rack L accommodated in the right table 21 to position the rack L at a predetermined position of the rack transporting portion 23 so that the sample tube T or the washing fluid tube C is supplied to the measurement units 31, 32. The transportation unit 2 also transports the rack L on the rack transporting portion 23 to the left table 22. The rack L is thus transported from the right table 21 towards the left table 22. In such transportation path, the direction of approaching the right table 21 is referred to as "upstream in transporting direction", and the direction of approaching the left table 22 is referred to as "downstream in transporting direction".

In the present embodiment, tubes accommodated in the rack L are retrieved and processed by the measurement unit 31, 32 in an order of arrangement from the downstream side in the transporting direction at the retrieving position P31a or P32a (see FIG. 4) of the rack transporting portion 23.

Figure 2A:
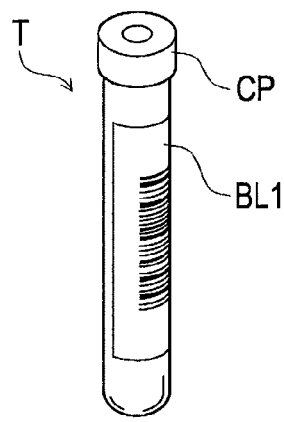
FIG. 2A is a view showing a configuration of a sample tube according to the embodiment.
Figure 2B:
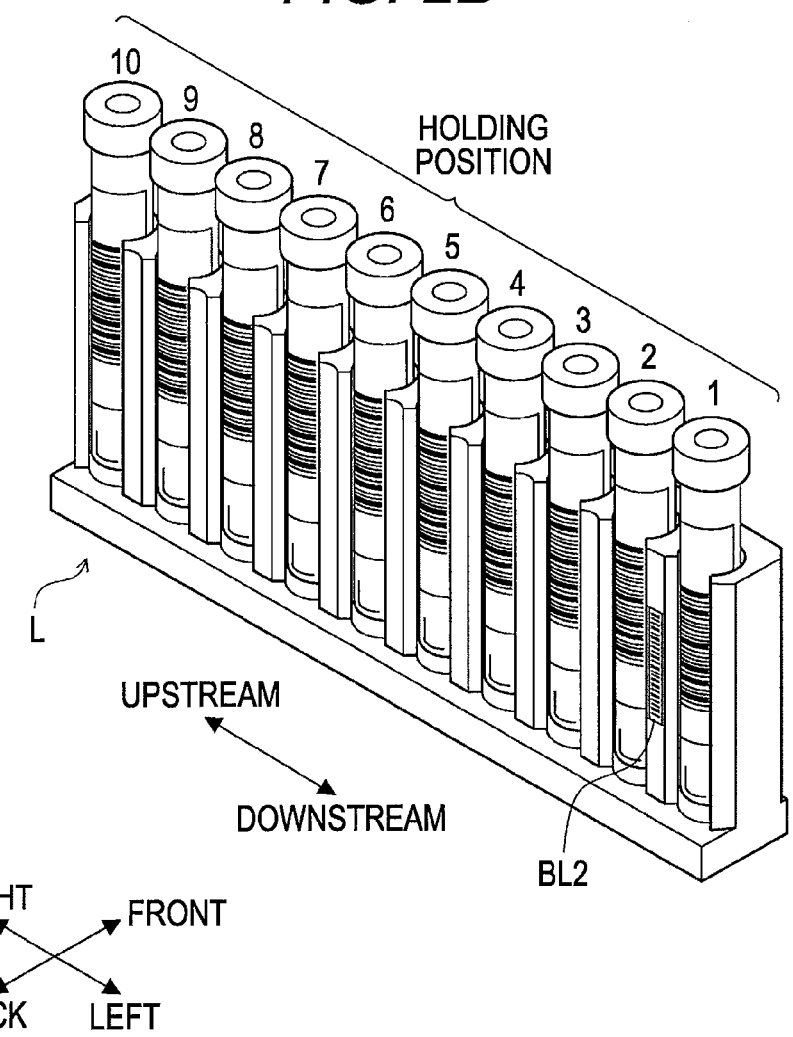
FIG. 2B is a view showing a configuration of a rack according to the embodiment.

FIG. 2A is a perspective view showing an outer appearance of the sample tube T, and FIG. 2B is a perspective view showing an outer appearance of the rack L holding ten sample tubes T. In FIG. 2B, the direction (front, back, left and right in FIG. 1, and upstream and downstream in the transporting direction) when the rack L is mounted on the transportation unit 2 is also shown.

With reference to FIG. 2A, the sample tube T is a tube made of glass or synthetic resin having translucency, and has an upper opening. A blood sample of whole blood collected from a patient is accommodated inside, and the opening at the upper end is sealed with a cap CP made of rubber. A barcode label BL1 is attached to a side surface of the sample tube T. A barcode including a sample ID is printed on the barcode label BL1.

With reference to FIG. 2B, the rack L is formed with ten holders at holding positions 1 to 10, as shown in the figure, to hold ten sample tubes T in a perpendicular state (standing state). For the sake of convenience, each holding position is assigned with a number in ascending order from the downstream towards the upstream in the transporting direction.

A barcode label BL2 is attached to a side surface on the back side of the rack L, as shown in the figure. A barcode including a rack ID is printed on the barcode label BL2.

Figure 3A:
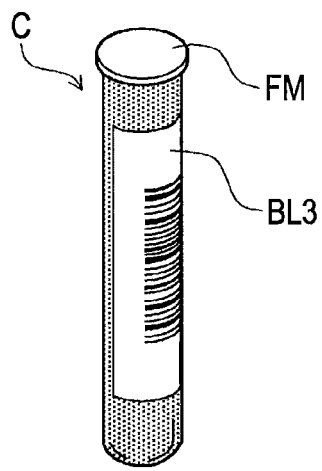
FIG. 3A is a view showing a washing fluid tube according to the embodiment.
Figure 3B:
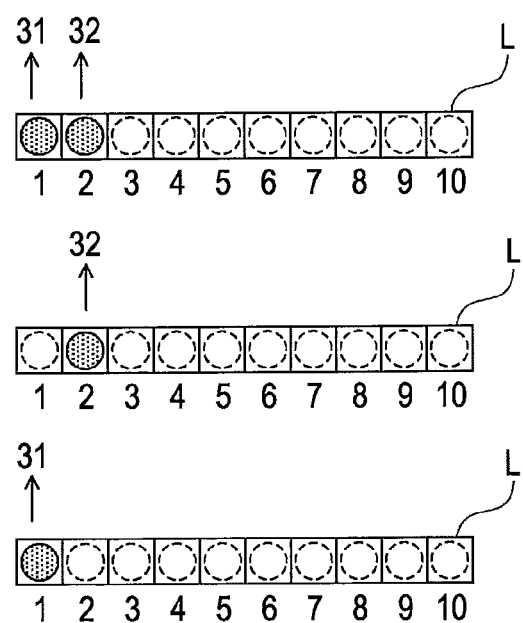
FIG. 3B is a view showing an arrangement rule of the washing fluid tube according to the embodiment.

FIGS. 3A and 3B are views showing a washing fluid tube C and an arrangement rule on the rack L of the washing fluid tube C. FIG. 3A is a perspective view showing an outer appearance of the washing fluid tube C, and FIG. 3B is a view showing the arrangement of the washing fluid tube C when the rack L is seen from the upper side. In FIG. 3B, the upstream and downstream in the transporting direction, and the numbers of the holding positions of the rack L are shown in a manner similar to FIG. 2B.

With reference to FIG. 3A, the washing fluid tube C is a tube made of glass or synthetic resin, and has an upper opening. Chlorine washing fluid for washing the fluid circuit in the measurement units 31 and 32 is accommodated inside the washing fluid tube C, and the opening at the upper end is sealed with a film FM to prevent a lowering of chlorine concentration in the washing fluid.

A barcode label BL3 is attached to a side surface of the washing fluid tube C. A barcode including a washing fluid ID is printed on the barcode label BL3. The washing fluid ID can be distinguished from the sample ID. The washing fluid tube C has similar shape and size as the sample tube T, and is held in a perpendicular state (standing state) in the rack L, similar to the sample tube T.

With reference to FIG. 3B, the washing fluid tube C is installed in the rack L according to a predetermined arrangement rule. The washing fluid tube C is installed from the downstream side in the transporting direction so that the washing operation can be initiated as soon as possible. The measurement unit to be washed is defined by the holding position where the washing fluid tube C is installed.

When washing both the measurement unit 31 and the measurement unit 32, the washing fluid tube C is installed at the holding position 1 and the holding position 2, as shown in the upper level of FIG. 3B. Neither the sample tube T nor the washing fluid tube C is normally installed at the other holding positions 3 to 10. In this case, the washing fluid tube C at the holding position 1 is allocated to the measurement unit 31, and the washing fluid tube C at the holding position 2 is allocated to the measurement unit 32.

When washing only the measurement unit 32, the washing fluid tube C is installed only at the holding position 2, as shown in the middle level of FIG. 3B, and when washing only the measurement unit 31, the washing fluid tube C is installed only at the holding position 1, as shown in the lower level of FIG. 3B. In such cases, the washing fluid tube C is allocated to one of the measurement units 31, 32.

Therefore, when washing the measurement units 31, 32, only the washing fluid tube C is normally installed at either one of or both of the holding position 1 and the holding position 2 of the rack L.

Returning back to FIG. 1, at the time of measuring sample, the measurement unit 31 performs the process on the sample tube T on the rack transporting portion 23. In other words, at the retrieving position P31a (see FIG. 4) of the rack transporting portion 23, the measurement unit 31 takes out the sample tube T from the rack L and transports it to the inside of the measurement unit 31 with a hand portion 31a (see FIG. 4) and aspirates the sample in the sample tube T. After aspiration is completed, the measurement unit 31 returns the sample tube T again back to the holder of the original rack L. The measurement unit 32 also performs the measurement of the sample similar to the measurement unit 31.

At the time of washing, the measurement unit 31 performs the process on the washing fluid tube C on the rack transporting portion 23. Similar to the manner of measuring the sample tube T, at the retrieving position P31a (see FIG. 4) of the rack transporting portion 23, the measurement unit 31 takes out the washing fluid tube C from the rack L and transports it to the inside of the measurement unit 31 with a hand portion 31a (see FIG. 4). The measurement unit 31 then aspirates the washing fluid in the washing fluid tube C and causes it flow to the flow path and the detector used for the measurement of the sample in the measurement unit 31, and retains the washing fluid thereat for a predetermined time to remove the dirt.

The washing process is carried out about once a day. In order to prevent a residual of dirt to accumulate in the fluid circuit, the washing fluid is retained in the fluid circuit for a long period of time. After the aspiration of the washing fluid is completed, the measurement unit 31 returns the washing fluid tube C again back to the holder of the original rack L. The measurement unit 32 also performs the washing similar to the measurement unit 31. Thereafter the powers of the washed measurement units 31, 32 are automatically shut down.

The information processing unit 4 includes an input section 41 and a display section 42. The information processing unit 4 is communicably connected to the transportation unit 2, the measurement units 31, 32 and a host computer 5 (see FIG. 8) through a communication network.

The information processing unit 4 controls the operations of the transportation unit 2 and the measurement units 31, 32. The information processing unit 4 makes an inquiry of a measurement order to the host computer 5 (see FIG. 8) when sample ID is read by the barcode unit B2 (see FIG. 4). The information processing unit 4 performs an analysis based on the measurement result of the measurement units 31, 32 and transmits the analysis result to the host computer 5 (see FIG. 8). The host computer 5 is configured to determine whether a sample needs a retest or not on the basis of the analysis result of the sample and transmit the determination result to the information processing unit 4. The information processing unit 4 acquires the determination result transmitted from the host computer 5 (see FIG. 8).

The retest of the sample performed after the measurement of the sample is hereinafter simply referred to as "retest". In the present embodiment, the retest will be described as being performed only once.

As will be described later, the information processing unit 4 displays predetermined information such as a warning message on the display section 42.

Figure 4:
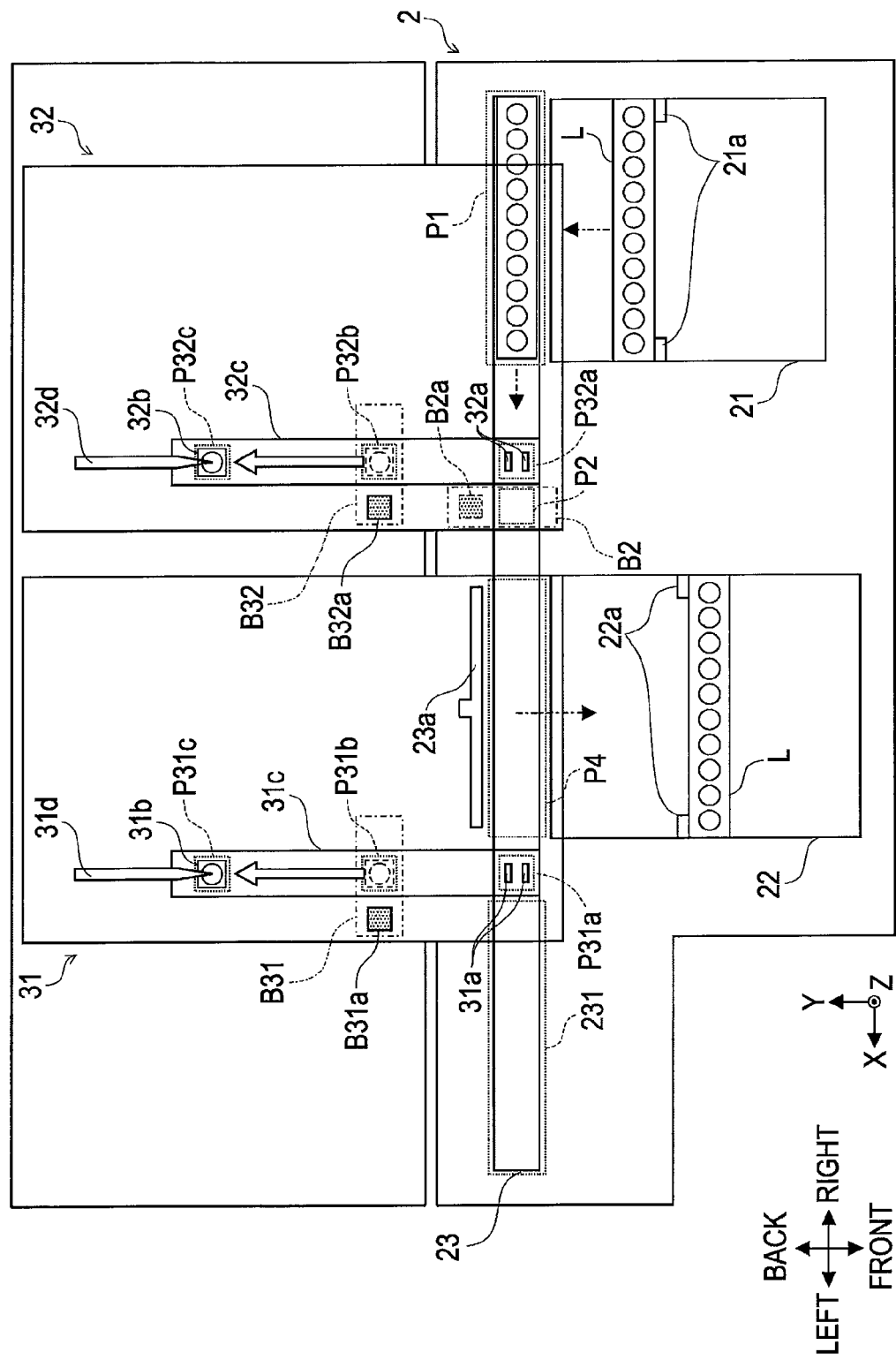
FIG. 4 is a plan view showing a configuration of a transportation unit and a measurement unit seen from an upper side according to the embodiment.

FIG. 4 is a view schematically showing a configuration of transportation unit 2 and the measurement units 31, 32 in a plan view.

First, the reading operation of the barcode information will be described with reference to FIG. 4.

The rack feeding mechanism 21a pushes the side surface on the front side of rack L, thereby the rack L set on the right table 21 is transported to a feeding position P1 at the right end of the rack transporting portion 23. The rack L positioned at the feeding position P1 of the rack transporting portion 23 is transported to the left direction by a belt (not shown) of the rack transporting portion 23. Two belts of the rack transporting portion 23 are arranged in parallel, where two racks L can be independently transported in the left and right direction by each belt.

A barcode unit B2 including a barcode reader B2a is installed near the middle of the rack transporting portion 23. When the holder of the rack L is positioned at the reading position P2 on the front side of the barcode reader B2a, whether or not the tube (sample tube T or washing fluid tube C) is held in the holder is determined by a holding determination mechanism (not shown) of the barcode unit B2. Such holding determination mechanism includes a mechanism capable of sandwiching the tube from two opposite sides from the front and back directions (Y axis direction). If the tube can be sandwiched, it is determined that a tube is held in the holder positioned at the reading position P2.

If the tube held in the holder is a sample tube T, the sample ID is read from the barcode label BL1 of the sample tube T by the barcode reader B2a while the sample tube T is rotated. If the tube held in the holder is a washing fluid tube C, the washing fluid ID is read from the barcode label BL3 of the washing fluid tube C by the barcode reader B2a while the washing fluid tube C is rotated. When the barcode label BL2 of the rack L is positioned on the front side of the barcode reader B2a, the rack ID is read from the barcode label BL2 of the rack L by the barcode reader B2a.

The barcode information of the rack L and the tube presence/absence information and the barcode information on all the holders at the holding positions 1 to 10 of the rack L are acquired in such manner.

The supplying operation of the sample tube T and the washing fluid tube C of the rack L to the measurement units 31, 32 will now be described.

After reading of the barcode information for each sample tube is completed, the sample tubes T installed in the holder of the rack L are supplied to the measurement unit 31 or the measurement unit 32 in an order from the tube arranged at the holding position on the downstream (left direction) in the transporting direction. For instance, if sample tubes T1, T2, and T3 are installed in the holding positions 1, 2, and 3 of the rack L, the sample tube T1 is first positioned at the retrieving position P31a. The measurement unit 31 is provided with the hand portion 31a arranged at the retrieving position P31a in a movable manner in the up and down direction (Z axis direction). The sample tube T1 positioned at the retrieving position P31a is gripped by the hand portion 31a, taken out from the rack L in the upward direction (positive direction in Z axis), and retrieved into the measurement unit 31.

After the sample tube T1 is taken out by the measurement unit 31, the sample tube T2 is positioned at the retrieving position P32a during the aspiration of the sample in the measurement unit 31. The sample tube T2 positioned at the retrieving position P32a is gripped by the hand portion 32a, taken out from the rack L in the upward direction (positive direction in Z axis), and retrieved into the measurement unit 32.

Thereafter, when the aspiration of the sample of the sample tube T1 is completed in the measurement unit 31, the holding position 1 where the sample tube T1 has been originally arranged is again positioned at the retrieving position P31a. The sample tube T1 is then returned to the holding position 1 of the rack L from the upward direction (position direction in Z axis).

The measurement unit 31 thus becomes vacant, and the sample tube T3 is then positioned at the retrieving position P31a and taken into the measurement unit 31.

Thus, sample tubes T on the rack L are supplied to the measurement units 31, 32 according to a predetermined rule where sample tubes T held at the odd-numbered holding positions are supplied to the retrieving position P31a and the sample tubes T held at the even-numbered holding positions are supplied to the retrieving position P32a.

After the measurement and the analysis, it may be turned out that a retest of the measured sample is necessary. In this case, the sample tube T accommodating the sample that needs a retest is supplied to one of the measurement units in preference to the non-measured sample tube T.

The supply of the washing fluid tube C to the measurement units 31, 32 follows the arrangement rule shown in FIG. 3B. The washing fluid tube C at the holding position 1 is first positioned at the retrieving position P31a and taken out by the measurement unit 31. The washing fluid tube C of the holding position 2 is then positioned at the retrieving position P32a, and taken out by the measurement unit 32.

Therefore, the washing fluid tube C installed in the rack L is supplied to the measurement units 31, 32 according to the arrangement rule shown in FIG. 3B by the rack transporting portion 23.

When the sample tube T is positioned at the retrieving positions P31a or P32a, the sample tube T is automatically retrieved into the measurement units 31 or 32 and the measurement of the sample is carried out. When the washing fluid tube C is positioned at the retrieving positions P31a or P32a, the washing fluid tube C is automatically retrieved into the measurement units 31 or 32 and the washing of the fluid circuit is carried out. Such operation is carried out under the control of the CPU 401 (see FIG. 8), to be described later.

FIG. 5A is a flowchart showing the retrieving operation of the sample tube T by the measurement units 31, 32. Hereinafter, an operation of the measurement unit 31 is described as a representative of the measurement units 31, 32.

With reference to FIG. 4 and FIG. 5A, when a sample tube T is positioned at the retrieving position P31a, the sample tube T is gripped by the hand portion 31a and taken out in the upward direction (positive direction in Z axis) (S31). The hand portion 31a then moves the sample tube T like a pendulum to stir the sample (S32). In this case, the tube setting portion 31b is moved to the front side (negative direction in Y axis) to be positioned above the retrieving position P31a (S33). After finishing the stirring, the hand portion 31a is moved in the downward direction (negative direction in Z axis), and the sample tube T gripped by the hand portion 31a is set in the tube setting portion 31b (S34).

Thereafter, the tube setting portion 31b is transported to the barcode reading position P31b (S35), and the sample tube T is checked by the barcode unit B31 including the barcode reader B31a (S36).

The tube setting portion 31b is then positioned at the aspirating position P31c at immediately below the piercing pipette 31d (S37). The piercing pipette 31d is then moved in the downward direction, and the sample is aspirated from the sample tube T positioned at the aspirating position P31c (S38).

After the aspiration of the sample by the piercing pipette 31d is finished, the tube setting portion 31b is moved to the front side and again positioned above the retrieving position P31a (S39). Above the retrieving position P31a, the sample tube T is taken out in the upward direction by the hand portion 31a from the tube setting portion 31b (S40). The tube setting portion 31b is then moved to the back side. Thereafter, the hand portion 31a is moved in the downward direction (negative direction in Z axis), and the sample tube T is returned to the original holder of the rack L positioned in the rack transporting portion 23 (S41).

FIG. 5B is a flowchart showing a retrieving operation of the washing fluid tube C by the measurement unit 31, 32. Hereinafter, an operation of the measurement unit 31 is described as a representative of the measurement units 31, 32.

In FIG. 5B, S51, and S52 to S60 are the same as S31, and S33 to S41 of FIG. 5A other than that the tube to be processed is a washing fluid tube C. Thus, the description of each step will be omitted herein. In the retrieving operation of FIG. 5B, the step corresponding to S32 of FIG. 5A is skipped. This is because the tube is the washing fluid tube C and the stirring operation is unnecessary.

In a case where the samples are measured, the sample tube T may possibly be supplied to the measurement unit 31 or 32 again for retest even after the aspirations of all the samples are completed and all the sample tubes T are returned to the holders of the rack L. Normally, the time required for determination of the necessity of retest is longer than the time required for completing the measurement of one sample due to the communication of the measurement result to the information processing unit 4 and the host computer 5, the analyzing process of the measurement result, and the like (e.g., the measurement time required for one sample is about 36 seconds, the time required for determining the necessity of retest is about 75 seconds).

A transportation space 231 longer than a length in the left and right direction of the rack L is provided in the left side of the retrieving position P31a of the rack transporting portion 23. The rack L is positioned in the transportation space 231 until the determination of necessity of retest for all the sample tubes T is completed. Thereby a space allowing to move the following rack on the rack transportation path is obtained.

After the process related to the retest is completed for all the sample tubes T, the rack L is positioned at the backward position of the left table 22, and transported to the front side of the left table 22 by a rack feeding mechanism 22a.

If the washing fluid tube C is held in the rack L, the washing liquid is aspirated for all the washing liquid tubes C, and thereafter, the rack L is positioned at the backward position of the left table 22, and transported to the front side of the left table 22 by the rack feeding mechanism 22a.

In such a manner, the measuring process or the washing process is performed for all the racks L present at the right table 21.

Figure 6:
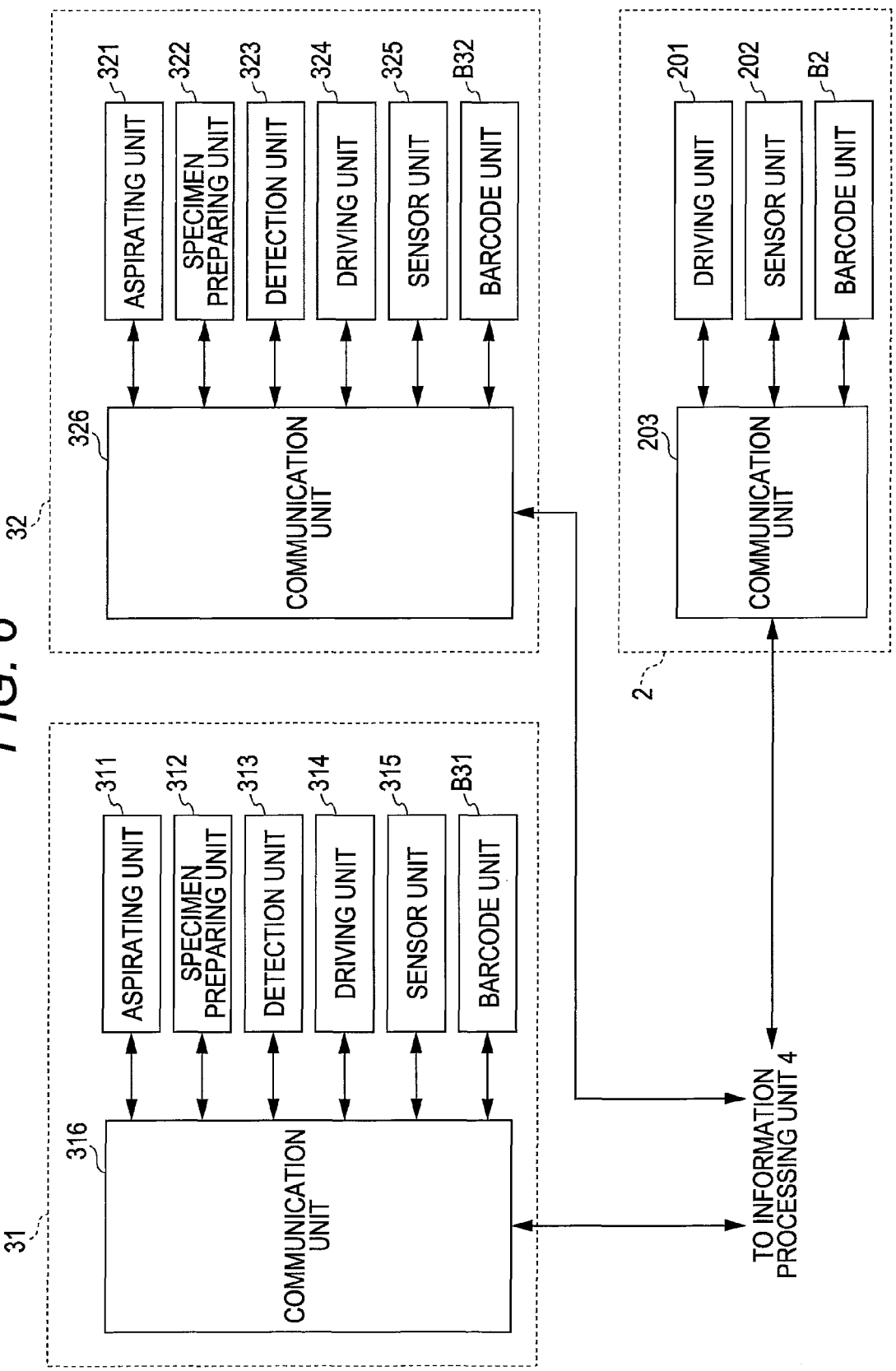
FIG. 6 is a view showing a block diagram of the transportation unit and the measurement unit according to the embodiment.

FIG. 6 is a view showing an electrical connection relationship of the transportation unit 2 and the measurement unit 31, 32.

The transportation unit 2 includes a driving unit 201, a sensor unit 202, a barcode unit B2, and a communication unit 203.

The driving unit 201 includes a mechanism for transporting the rack L in the transportation unit 2, and the sensor unit 202 includes a sensor for detecting the rack L at a predetermined position on a transportation path of the transportation unit 2. As described above, the barcode unit B2 includes the holding determination mechanism (not shown), and a barcode reader B2a.

The communication unit 203 is communicably connected with the information processing unit 4. Each section of the transportation unit 2 is controlled by the information processing unit 4 through the communication unit 203. A signal output from each section of the transportation unit 2 is transmitted to the information processing unit 4 through the communication unit 203.

The measurement units 31, 32 respectively include an aspirating unit 311, 321, a specimen preparing unit 312, 322, a detection unit 313, 323, a driving unit 314, 324, a sensor unit 315, 325, a barcode unit B31, B32, and a communication unit 316, 326. The measurement units 31, 32 have exactly the same configuration, and thus only the measurement unit 31 will be described below.

Figure 7:
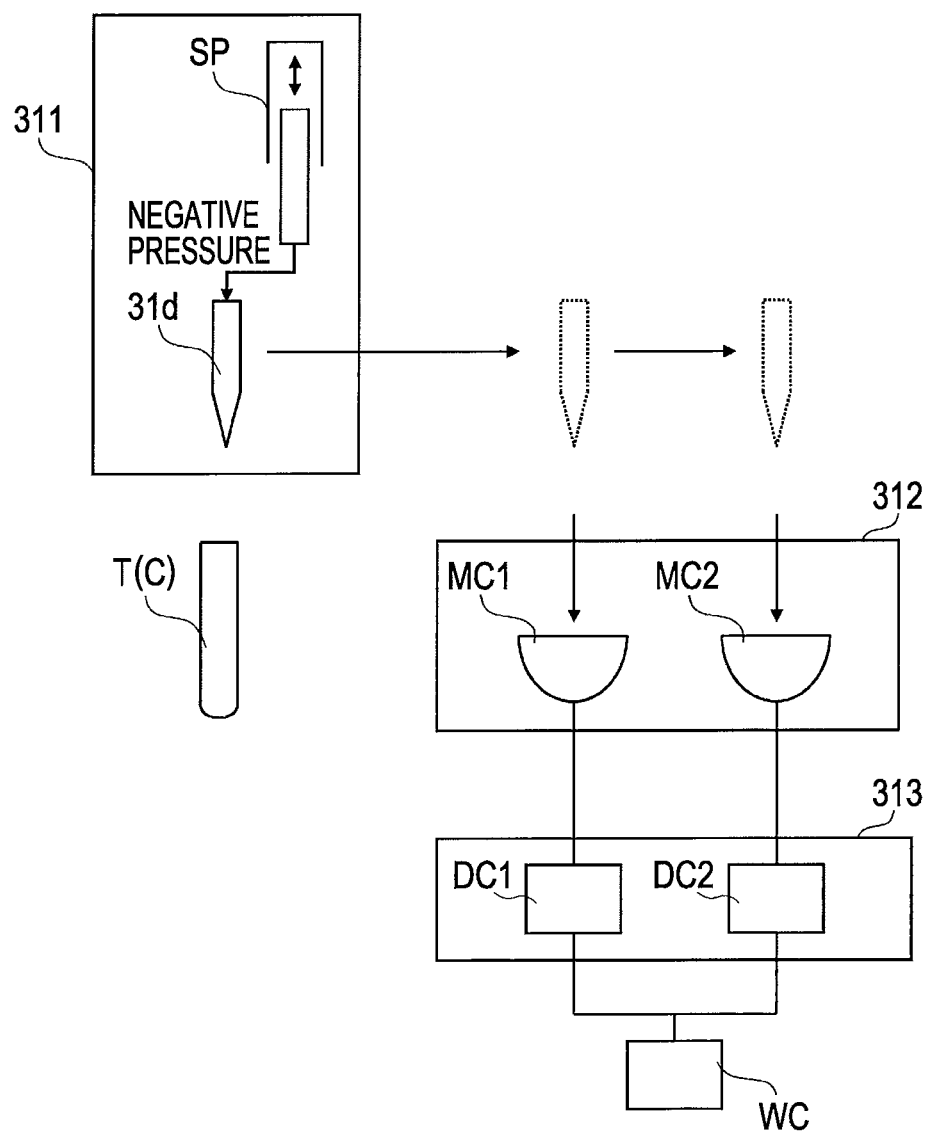
FIG. 7 is a view showing an outline of a fluid circuit of the measurement unit according to the embodiment.

FIG. 7 is a view showing an outline of a fluid circuit of the measurement unit 31. The measurement unit 31 is a blood cell counter, and can count blood cells contained in a blood sample of a whole blood accommodated in a sample tube T.

The aspirating unit 311 includes a piercing pipette 31d for aspirating a sample contained in a sample tube T and a washing fluid contained in a washing fluid tube C taken into the measurement unit 31. Thereafter the piercing pipette 31d is inserted to the tube, and a negative pressure generated by a syringe pump SP is applied to the piercing pipette 31d. The specimen preparing unit 312 includes a reaction chamber MC1 for preparing a specimen for measuring red blood cells and blood platelets, and a reaction chamber MC2 for preparing a specimen for measuring white blood cells. The detection unit 313 includes an electrical resistance detector DC1 for measuring red blood cells and blood platelets, and an optical detector DC2 for optically measuring white blood cells. The measurement unit 31 includes a waste chamber WC containing waste fluid.

When measuring the sample accommodated in the sample tube T, the aspirating unit 311 aspirates the sample through the piercing pipette 31d by applying negative pressure to the piercing pipette 31d with the syringe pump SP, and discharges the sample to each reaction chamber MC1 and MC2. The specimen preparing unit 312 mixes the sample and a reagent in the reaction chamber MC1 to prepare a specimen for measuring red blood cells and blood platelets. The specimen preparing unit 312 mixes the sample and a reagent in the reaction chamber MC2 to prepare a specimen for measuring white blood cells. The specimen prepared in the reaction chamber MC1 is supplied to the electrical resistance detector DC1 through the flow path, and the specimen prepared in the reaction chamber MC2 is supplied to the optical detector DC2 through the flow path. The detection unit 313 detects optical information (side fluorescent signal, forward scattered light signal, side scattered light signal, etc.) from white blood cells, nucleated red blood cells, and the like in the specimen as data of the sample with the optical detector DC2. The detection unit 313 also detects electrical information from the red blood cells and the blood platelets in the specimen as data of the sample with the electrical resistance detector DC1. The specimen that passed the detection unit 313 is supplied to the waste chamber WC through the flow path.

When performing washing using the washing fluid contained in the washing fluid tube C, the washing fluid is sent along the path similar to the sample. That is, washing fluid is aspirated from the washing fluid tube C by the aspirating unit 311 and discharged to each reaction chamber of the specimen preparing unit 312, so that the path from each reaction chamber to the waste chamber WC is filled with washing fluid. It is left untouched in this state for a long time, and thereby residues of the sample or the reagent attached to the inner wall of the reaction chamber are removed.

Returning back to FIG. 6, the driving unit 314 includes a mechanism for transporting the sample tube T and the washing fluid tube C in the measurement unit 31. The sensor unit 315 includes a sensor for detecting the sample tube T or the washing fluid tube C at a predetermined position on the transportation path of the measurement unit 31. As described above, the barcode unit B31 includes the holding determination mechanism (not shown) and a barcode reader B31a.

The communication unit 316 is communicably connected with the information processing unit 4. Each section of the measurement unit 31 is controlled by the information processing unit 4 through the communication unit 316. A signal output from each section of the measurement unit 31 is transmitted to the information processing unit 4 through the communication unit 316.

Figure 8:
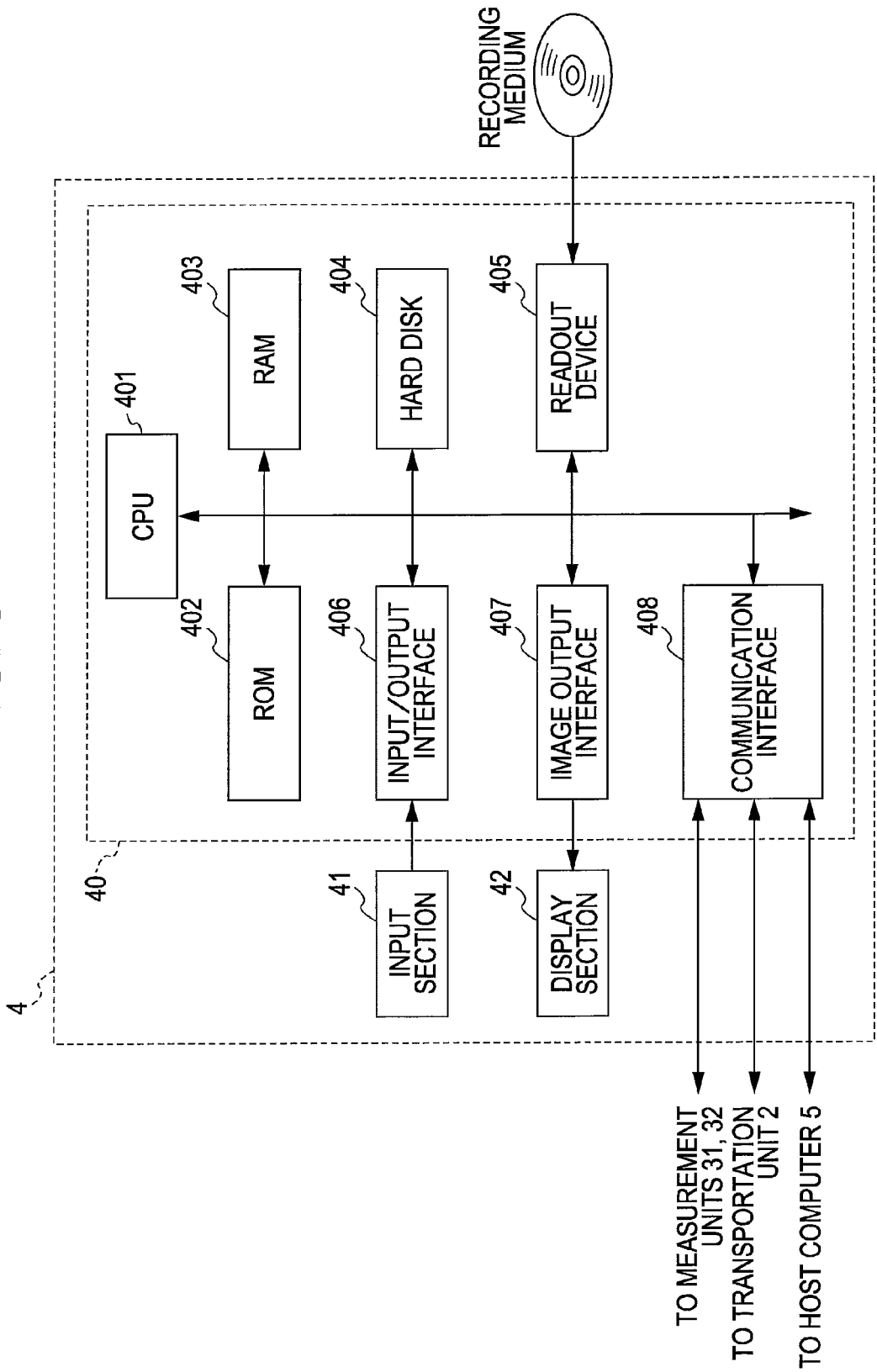
FIG. 8 is a view showing a block diagram of an information processing unit according to the embodiment.

FIG. 8 is a view showing a configuration of the information processing unit 4.

The information processing unit 4 includes a personal computer and is configured by the main body 40, the input section 41, and the display section 42. The main body 40 includes a CPU 401, a ROM 402, a RAM 403, a hard disk 404, a readout device 405, an input/output interface 406, an image output interface 407, and a communication interface 408.

The CPU 401 can execute computer programs stored in the ROM 402 and the computer programs loaded in the RAM 403. The RAM 403 is used to read out the computer programs recorded on the ROM 402 and the hard disk 404. In executing the computer programs, the ROM 403 is used as a work area of the CPU 401.

The hard disk 404 is installed with various computer programs to be executed by the CPU 401 such as operating system and application program, as well as data used in executing the computer program. In other words, the hard disk 404 is installed with a program for analyzing the data of the sample transmitted from the measurement units 31, 32 to generate measurement results of the number of red blood cells, the number of white blood cells, and the like, and making a display on the display section 42 based on the generated measurement results. The hard disk 404 is also installed with a program for displaying an operation screen M1, a help dialogue D1 for displaying a warning message, and the like, to be described later, and accepting the input through such screens.

The readout device 405 includes a CD drive or DVD drive, and is capable of reading out a computer program or data recorded in a recording medium. The input section 41 including a mouse and a keyboard connected to the input/output interface 406, where the user uses the input section 41 to input instructions and data to the information processing unit 4. The display section 42 including a display connected to the image output interface 407, where a video signal corresponding to the image data is output to the display section 42.

The display section 42 displays the image based on the input video signal. Various types of program screens are displayed on the display section 42 other than the operation screen M1 and the help dialogue D1 described later. The data is transmitted and received with respect to the transportation unit 2, the host computer 5 and the measurement units 31, 32 by the communication interface 408.

Figure 9:
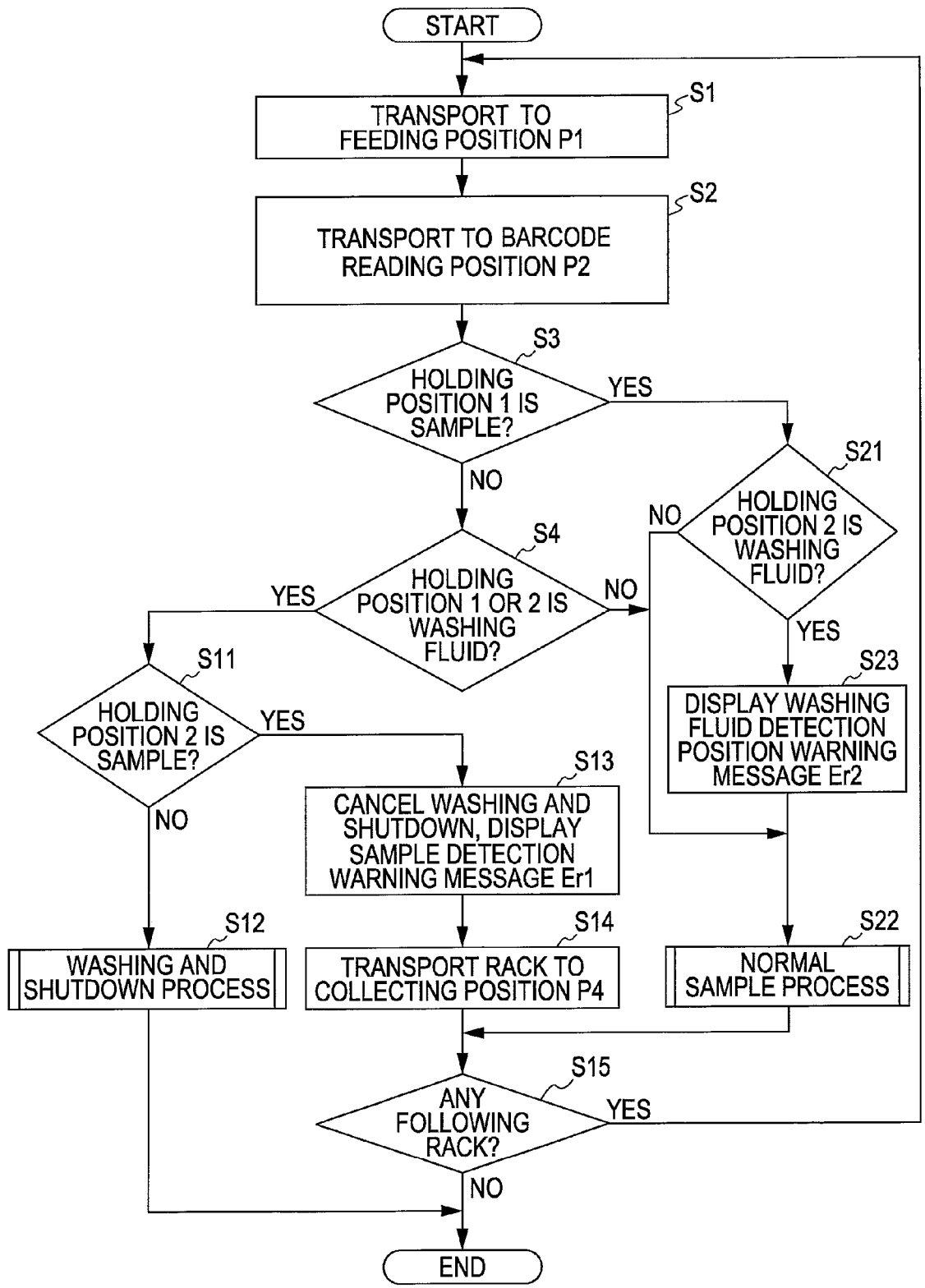
FIG. 9 is a view showing a flowchart of transportation control of the rack according to the embodiment.

FIG. 9 is a flowchart showing a flow of the control operation of the rack L by the CPU 401 of the information processing unit 4.

First, whether to perform the washing and shutdown process or to perform the sample process is determined for the rack L according to the type of tube arranged in the holding positions 1 and 2 of the rack L.

Specifically, when the rack L is set in the right table 21, the CPU 401 operates the rack feeding mechanism 21a to transport the rack L to the feeding position P1 of the rack transporting portion 23 (S1). The CPU 401 operates the rack transporting portion 23 to transport the rack L so that the holding positions 1 and 2 of the rack L are positioned at the barcode reading position P2 (S2). Then, presence or absence of tube is determined for each of the holding positions 1 and 2, and the barcode information of the present tube is read by the barcode unit B2. The CPU 401 then determines whether a sample tube T is present at the holding position 1 (S3). If not (S3: NO), the CPU 401 determines whether or not a washing fluid tube C is present at the holding position 1 or 2 (S4). According to the determination result of steps S3 and S4, it is determined whether the washing and shutdown process shall be carried out for the rack L, or the sample process shall be carried out for the rack L.

If sample tube T is not at the holding position 1 (S3: NO) and washing fluid tube C is at the holding position 1 or 2 (S4: YES), the CPU 401 further determines whether sample tube T is at the holding position 2 (S11). If sample tube T is not at the holding position 2 (S11: NO), the arrangement of tubes in the holding positions 1 and 2 is in conformity with the normal arrangement rule of the washing fluid tube C shown in FIG. 3B. In this case, the CPU 401 executes the washing and shutdown process, and executes a process corresponding to the presence or absence of the tube at the holding positions 3 to 10 following the holding positions 1 and 2 (S12). The details on the washing and shutdown process (S12) will be described later with reference to FIG. 11.

Figure 10A:
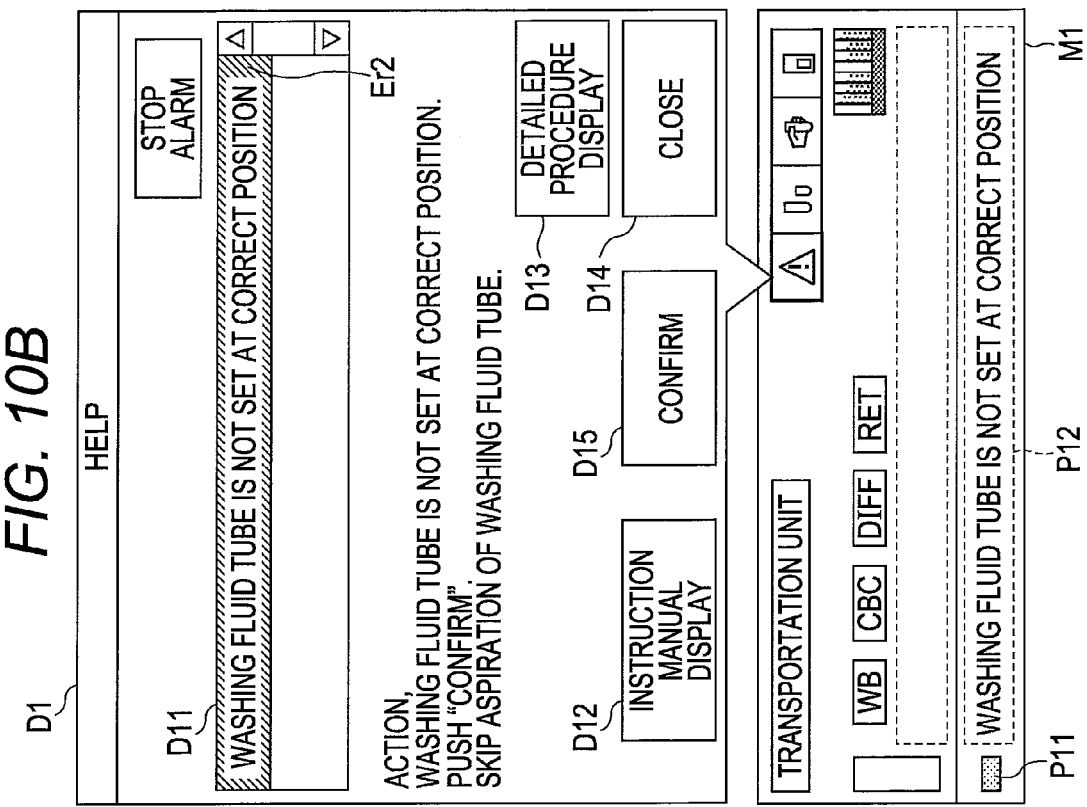
FIG. 10A is a view showing an example screen according to the embodiment.

If determined that the sample tube T is at the holding position 2 in S11 (S11: YES), this means that the washing fluid tube C is at the holding position 1 and the sample tube T is at the holding position 2. In this case, the CPU 401 cancels the washing and shutdown process, and displays the help dialogue D1 on the operation screen M1 of the display section 42 to display a sample detection warning message Er1 as shown in FIG. 10A. (S13)

FIG. 10A shows the operation screen M1 and the help dialogue D1 displayed when the sample detection warning message Er1 is displayed.

In the operation screen M1, the color of a status notifying section P11 is changed from green, which indicates a normal status, to red, which indicates a status where an error occurred, since the sample is detected at the following holding position of the washing fluid tube C. A message "tube other than washing fluid tube is set" is displayed in an error message display region P12 as the sample detection warning message Er1. The help dialogue D1 is displayed at the upper part of the operation screen M1.

In the help dialogue D1, an error message list D11, an instruction manual display button D12, a detailed procedure display button D13, a close button D14, and a confirm button D15 are displayed. An error message similar to the error message display region P12 of the operation screen M1 is displayed in the error message list D11. A message suggesting the operator to check the arrangement of tubes of the rack L and to push the confirm button D15 is displayed as an operation of when the sample detection warning message Er1 is displayed in the lower action column of the error message list D11.

When the instruction manual display button D12 is pushed, a page of an electronic manual is displayed. The page includes information relating an error such as causes of the error, ways to recover the error, conditions for recovering the error, and the like. When the detailed procedure display button D13 is pushed, a page of the electronic manual is displayed. The page includes countermeasure method (operation procedure) for the sample detection warning message Er1. When the close button D14 is pushed, the help dialogue D1 is closed. When the confirm button D15 is pushed, the process proceeds to S14 of FIG. 9.

Returning back to FIG. 9, when the confirm button D15 in the help dialogue D1 is pushed, the CPU 401 operates the rack transporting portion 23 to transport the rack L to the collecting position P4 (S14).

The CPU 401 then determines whether or not the following rack L is in the right table 21 (S15). If there is a following rack L (S15: YES), the process is returned to S1, and the processes described above are repeated. If there is no following rack L (S15: NO), the process is completed for all the racks L.

As seen from the above disclosures, the washing and shutdown process is not carried out if the washing fluid tube C is at the holding position 1 and the sample tube T is at the holding position 2 of the rack L. In other words, the rack L is discharged to the left table 22, and the supply of the washing fluid contained in the washing fluid tube C to the corresponding measurement unit is skipped. In this case, the measurement process of the sample tube T at the holding position 2 arranged in the same rack L is also skipped since the rack L is discharged to the left table 22.

If determined that the sample tube T is at the holding position 1 in S3 (S3: YES), the CPU 401 further determines whether the washing fluid tube C is at the holding position 2 (S21). If the washing fluid tube C is not present at the holding position 2 (S21: NO), it is assumed that the washing fluid tube C is not installed at least in the holding positions 1 and 2. In this case, the CPU 401 executes the normal sample process, and executes the process corresponding to the presence or absence of the tube at the holding positions 3 to 10 following the holding positions 1, 2 (S22). The details of the normal sample process (S22) will be described later with reference to FIG. 12.

If the sample tube T is not at the holding position 1 (S3: NO) and the washing fluid tube C is not at the holding position 1 or 2 (S4: NO), it is assumed that the tube is not at the holding position 1 and either the tube is not at the holding position 2 or the sample tube T is at the holding position 2. In this case as well, the washing fluid tube C is not installed at least the holding positions 1, 2, and hence the CPU 401 executes the normal sample process (S22).

Figure 10B:
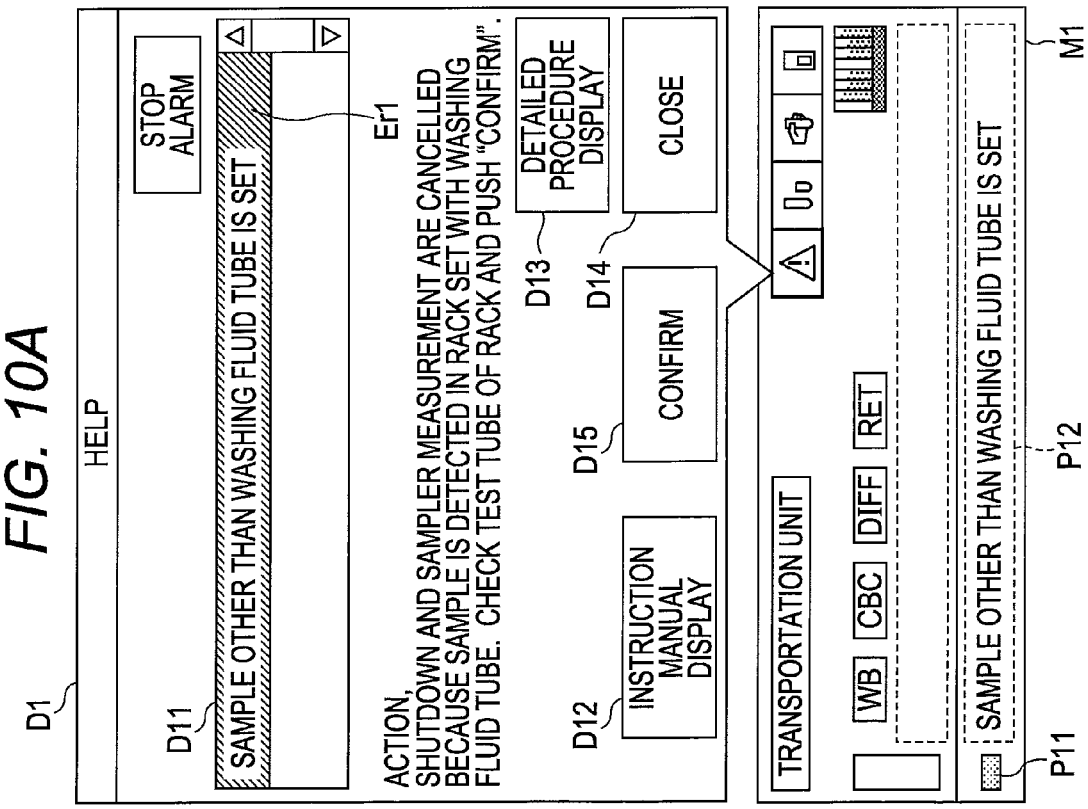
FIG. 10B is a view showing an example screen according to the embodiment.

If the sample tube T is at the holding position 1 (S3: YES) and the washing fluid tube C is at the holding position 2 (S21: YES), the CPU 401 displays the help dialogue D1 on the operation screen M1 of the display section 42 and displays a washing fluid detection position warning message Er2, as shown in FIG. 10B. (S23)

FIG. 10B shows the display content of the operation screen M1 and the help dialogue D1 for displaying the washing fluid detection position warning message Er2.

In the operation screen M1, the color of the status notifying section P11 is changed from green, which indicates a normal status, to red, which indicates a status where an error occurred, since an arrangement of the washing fluid tube C is not in conformity with the arrangement rule of the washing fluid tube C shown in FIG. 3B. A message "washing fluid tube is not set at correct position" is displayed as the washing fluid detection position warning message Er2 in the error message display region P12. The help dialogue D1 is displayed at the upper part of the operation screen M1.

An error message list D11 and various types of buttons are displayed similar to the screen shown in FIG. 10A. The operation of various types of buttons is similar to the screen shown in FIG. 10A. An error message similar to the error message display region P12 of the operation screen M1 is displayed in the error message list D11. When the confirm button D15 is pushed, a message guiding that the aspiration of the washing fluid tube C is skipped is displayed as an operation of when the washing fluid detection position warning message Er2 is displayed in the action column at the bottom of the error message list D11. When the confirm button D15 is pushed, the process proceeds to S22 of FIG. 9, and the CPU 401 executes the normal sample process (S22).

When a predetermined number of steps of the normal sample process S22 is completed with respect to the rack L, next rack L is allowed to be sent in the rack transporting portion 23. The CPU 401 determines whether there is a following rack in the right table 21 (S15). Specifically, the timing where the next rack L is allowed to be sent in is when it is determined that the preceding rack L does not need to be positioned at the position of the feeding position P1 of the rack transporting portion 23, that is when it is determined that a predetermined number of sample tubes T of the rack L are not required to be retested. For instance, if the necessity on the retest is acquired up to the sixth tube on the preceding rack L, the preceding rack L will not be returned to the position of the feeding position P1, and the following rack L is allowed to be positioned at the feeding position P1.

If there is a following rack L in such state (S15: YES), the process is returned to S1, so that the following rack L is transported to the feeding position P1, the above-described processes are repeated, and the sample process or the washing process is carried out.

If there is no following rack L (S15: NO), the process is completed for all the racks L.

Figure 11:
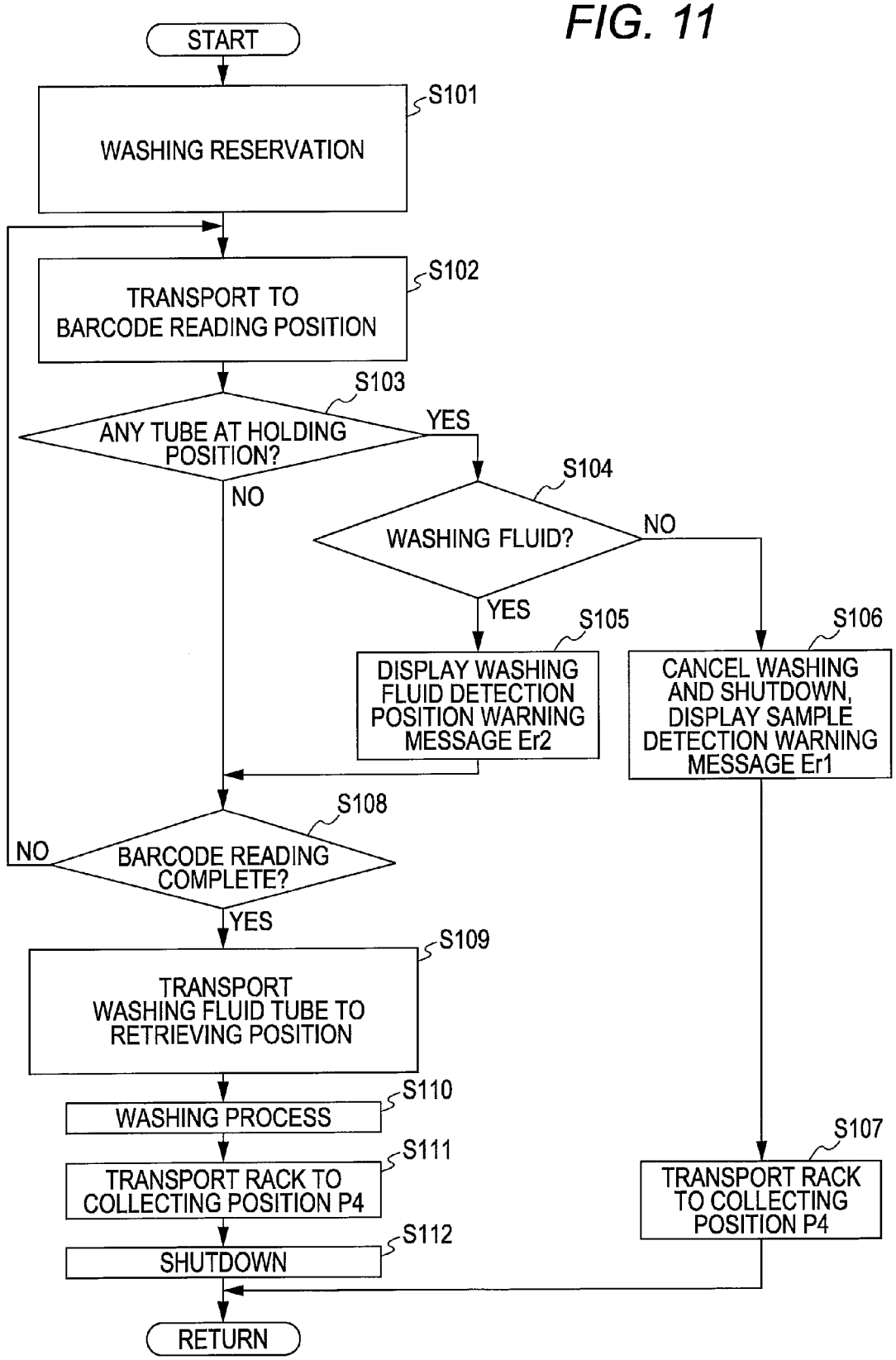
FIG. 11 is a view showing a flowchart of transportation control of the rack at time of washing and shutdown according to the embodiment.

FIG. 11 is a view showing a flowchart of the control operation of the rack L by the CPU 401 at the time of washing and shutdown process of S12 of FIG. 9.

When determined that tubes in the holding positions 1 and 2 of the rack L are in conformity with the normal arrangement rule of the washing fluid tube C shown in FIG. 3B, the CPU 401 performs a washing reservation of the measurement unit corresponding to the arrangement of the washing fluid tube C (S101). For instance, if the washing fluid tube C is set in both the holding position 1 and the holding position 2, the reservation for washing is made on the measurement units 31 and 32, whereas if the washing fluid tube C is set only in the holding position 1, the reservation for washing is made only on the measurement unit 31.

The CPU 401 then operates the rack transporting portion 23 to transport the rack L such that the following holding positions 3 to 10 are sequentially positioned at the barcode reading position P2 (S102). In this case, the presence or absence of the tube at each holding position is determined, and furthermore, the barcode information of the tube installed at each holding position is read by the barcode unit B2. The CPU 401 determines whether or not any tube is set at each holding position based on the result (S103). If any tube is not set at the holding positions 3 to 10 (S103: NO), the process proceeds to S108. If one or more tubes are set at any one of the holding positions 3 to 10 (S103: YES), the CPU 401 determines whether or not a washing fluid tube C is set (S104).

If a washing fluid tube C is set at the holding positions 3 to 10 (S104: YES), the CPU 401 determines that the arrangement of washing fluid tube C is not in conformity with the normal arrangement rule, and displays the washing fluid detection position warning message Er2 as shown in FIG. 10B (S105). When the confirm button D15 is pushed in the help dialogue D1 of the washing fluid detection position warning message Er2, the CPU 401 skips a process for the washing fluid tube C installed at the holding positions 3 to 10 and proceeds the process to S108.

If a washing fluid tube C is not set at the holding positions 3 to 10 (S104: NO), that is, if a sample tube T is set, the CPU 401 cancels the reserved washing and shutdown process, and displays the sample detection warning message Er1 as shown in FIG. 10A (S106). When the confirm button D15 is pushed in the help dialogue D1 of the sample detection warning message Er1, the CPU 401 operates the rack transporting portion 23 to transport the rack L to the collecting position P4 (S107). The rack L transported to the collecting position P4 is discharged to the left table 22 by a rack push-out mechanism 23a, whereby the process of the rack L is completed.

Therefore, even if the washing fluid tube C is arranged in conformity with the arrangement rule, if any sample tube T is at the following holding positions 3 to 10, the washing and shutdown process is not carried out. In this case, the measurement process of the sample tube T at the holding positions 3 to 10 arranged in the same rack L is also not carried out since the rack L is discharged to the left table 22. Furthermore, if the washing fluid tube C is arranged at the holding positions 3 to 10, processes for them will be skipped, and only the washing fluid tubes C correctly arranged according to the arrangement rule are used for the washing process (S110).

The processes described above are repeated until the reading of all the barcodes of the holding positions 3 to 10 is completed (S108: NO). After the reading of all the barcodes of the holding positions 3 to 10 is completed (S108: NO), the CPU 401 operates the rack transporting portion 23 to transport the washing fluid tube C to the retrieving positions P31a or P32a that corresponds to a measurement unit on which the washing is reserved (S109). In the measurement units 31 or 32 on which the washing is reserved, the washing process using the corresponding washing fluid tube C is carried out (S110). The washing process includes an operation of causing the washing fluid to fill a fluid circuit for a long time. It takes a long period of time (e.g., 30 minutes). After the washing process is completed, the CPU 401 operates the rack transporting portion 23 to transport the rack L to the collecting position P4 (S111). The rack L transported to the collecting position P4 is discharged to the left table 22 by the rack push-out mechanism 23a. Thereafter, the CPU 401 shuts down the measurement units 31, 32 and the information processing unit 4 (S112). If only one of the measurement units 31 and 32 is washed, the shutdown is not executed, and the shutdown will be executed at the timing the washing of both measurement units 31, 32 is completed. The washing process and the shutdown process of the measurement units are carried out in such a manner, and the process is completed.

Figure 12:
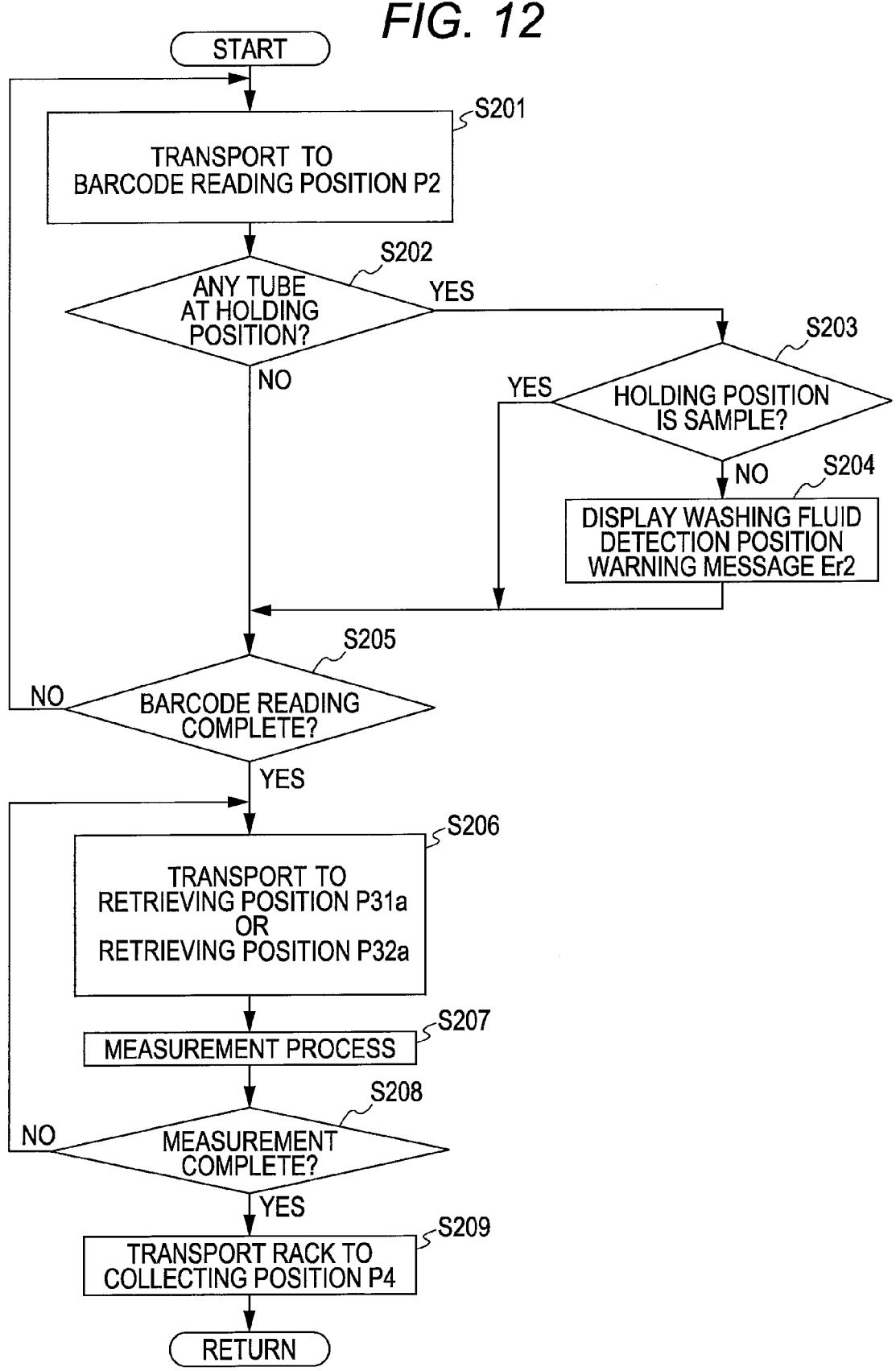
FIG. 12 is a view showing a flowchart of transportation control of the rack at time of normal sample processing according to the embodiment.

FIG. 12 is a view showing a flowchart of the control operation of the rack L by the CPU 401 at the time of the normal sample process of S22 of FIG. 9.

When determined that tubes in the holding positions 1 and 2 of the rack L are in conformity with the arrangement for performing the normal sample process by the process shown in FIG. 9, the CPU 401 operates the rack transporting portion 23 to transports the rack L such that the following holding positions 3 to 10 are sequentially positioned at the barcode reading position P2 (S201). The presence or absence of the tube at each of the holding positions 3 to 10 is determined, and furthermore, the barcode information of the tube installed at each holding position is read by the barcode unit B2. The CPU 401 determines whether or not the tube is set at each holding position based on the result (S202). If any tube is not set at the holding positions 3 to 10 (S202: NO), the process proceeds to S205. If one or more tubes are set at any one of the holding positions 3 to 10 (S202: YES), the CPU 401 determines on the basis of the barcode information whether or not the type of the tube is sample tube T (S203).

If the type of the tube is sample tube T (S203: YES), the process proceeds to S205. If the type of the tube is not sample tube T (S203: NO), that is, if the washing fluid tube C is set, the CPU 401 determines that the washing fluid tube C is installed at the holding positions in unconformity with the normal arrangement rule. Then CPU 401 displays the washing fluid detection position warning message Er2 as shown in FIG. 10B (S204). When the confirm button D15 in the help dialogue D1 is pushed, the CPU 401 skips a process for the washing fluid tube C and proceeds the process to S205.

Therefore, even if the washing fluid tube C is not at the holding positions 1, 2 of the rack L, if the following holding positions 3 to 10 are installed with the washing fluid tube C, the process for the washing fluid tube C is skipped. And only the correctly set sample tube T is processed by the measurement units 31, 32.

The processes described above are repeated until the reading of all the barcodes of the holding positions 3 to 10 is completed (S205: NO). After the reading of all the barcodes of the holding positions 3 to 10 is completed (S205: YES), the CPU 401 operates the rack transporting portion 23 to transports the sample tubes T to the retrieving position P3 1a or the retrieving position P32a (S206). As described above, the sample tubes T are allocated to the measurement units 31 and 32 in an order from the downstream in the transporting direction. While both measurement units 31 and 32 are in measurement, the supply of the sample tubes T is waited. If one holding position is not installed with tube or is installed with the washing fluid tube C, the process for the holding position is skipped. The measurement units 31 and 32 performs the measurement process using the transported sample tube T (S207), and performs a re-test process if required.

After the measurement process and the re-test process of the sample are completed, the CPU 401 determines whether or not the measurement and the re-test of the sample are completed for all the sample tubes T accommodated in the rack L (S208). If the measurement and the re-test of all the samples are not completed (S208: NO), the processes of S206, S207 are repeated. If the measurement and the re-test of all the samples are completed (S208: YES), the CPU 401 operates the rack transporting portion 23 to transports the rack L to the collecting position P4 (S209). The rack L transported to the collecting position P4 is discharged to the left table 22 by the rack push-out mechanism 23a, whereby the normal sample process with respect to the relevant rack L is completed.

FIG. 13 is a view showing a relationship of the warning messages and an arrangement of tubes.

As shown in FIG. 13A, even if the washing fluid tube C is held at the holding positions 1 or 2 according to the normal arrangement rule, if the sample tube T is arranged on the upstream side of the holding position of the washing fluid tube C, the sample detection warning message Er1 shown in FIG. 13D is displayed and the washing and shutdown process is canceled. In this case, the aspiration of the washing fluid contained in the washing fluid tube C is skipped, and the rack L is discharged to the left table 22. Therefore, the process on the sample tube T is also skipped.

As shown in FIG. 13B, if the washing fluid tube C is held at the holding positions 1 or 2 according to the normal arrangement rule and the washing fluid tube C is arranged further on the upstream side, the washing fluid detection position warning message Er2 shown in FIG. 13E is displayed. In this case, aspiration of washing fluid is carried out with respect to the washing fluid tube C set in the holding positions 1 or 2, but the processes of the washing fluid tubes C in the holding positions 3 to 10 are skipped.

As shown in FIG. 13C, if the sample tube T is installed at the downstream side and the washing fluid tube C is installed at the upstream side or the washing fluid tube C is arranged in unconformity with the arrangement rule, the washing fluid detection position warning message Er2 shown in FIG. 13E is displayed and the aspiration of all washing fluids is skipped. In this case, only the process for the sample tube T is executed.

In the present embodiment, when the washing and shutdown process is canceled, the washing fluid tube C is not positioned at the retrieving position P31a, P32a of the measurement unit 31, 32 and the rack L is transported to the collecting position P4.

According to the present embodiment, if a sample tube T and a washing fluid tube T are arranged such as the sample tube T follows the washing fluid tube C in an order of supplying the tubes to the measurement units, the supply of the washing fluid tube C to the measurement unit 31 or 32 is skipped. Hence the washing is avoided from being automatically started before the sample in the sample tube T is aspirated and processed by the measurement unit. This may avoids a situation where a sample needs to be processed has to wait until a washing operation that has been already started is completed.

According to the present embodiment, if the supply of the washing fluid tube C is skipped, the supply of the sample tube T is also skipped and the rack L is discharged to the left table 22. Therefore the user can determine whether to perform the process of the sample or to perform the process of washing and rearrange the tubes in the rack L.

According to the present embodiment, when skipping the process of washing fluid tube C, the sample detection warning message Er1 is displayed on the display section 42 of the information processing unit 4, so that the user can easily know that there is a defect in the arrangement of the washing fluid tube C.

Furthermore, according to the present embodiment, the measurement units 31, 32 are automatically shut down and the information processing unit 4 is also automatically shut down after the washing is executed, so that the user is not required to wait for a completion of the washing process that takes a long time in order to manually shut down the power of the apparatus. The trouble of the user thus can be alleviated.

The embodiment of the present invention has been described above, but the embodiment of the present invention is not limited thereto.

For instance, the sample analyzer 1 for performing the measurement and the analysis of the sample has been illustrated in the above described embodiment, but the present invention may also be applied to a sample processing apparatus in which only the measurement or the process of the sample is carried out.

In the above described embodiment, a blood cell counter is illustrated as the sample processing unit, type of the unit is not limited to the embodiment. The sample processing unit may be other type analyzer such as a urine analyzer or a blood coagulation analyzer. Or the sample processing unit may be a smear sample preparing apparatus.

In the above described embodiment, the measurement unit is configured to grip a sample tube by the hand portion, take it out from the rack and aspirate sample therein with the piercing pipette, but the configuration of the measurement unit is not limited to this. The measurement unit may be configured to aspirate a sample in the sample tube T while the sample tube T is held on the rack.

In the above described embodiment, the rack transporting portion 23 is controlled not to position the washing fluid tube C at the retrieving position P31a, P32a so that the supply of the washing fluid to the measurement unit 31, 32 is skipped, but other configuration may be used. For example, in order to skip the supply of the washing fluid to the measurement unit, the rack transporting portion 23 may be controlled to position the washing fluid tube C at the retrieving position P31a, P32a, but in such case the measurement unit will be controlled not to take the washing fluid tube C positioned at the retrieving position P31a, P32a into the measurement unit. As other configuration, the measurement unit may be controlled to take the washing fluid tube C into it, but in such case the tube transporting portion 31c, 32c will be controlled not to position the washing fluid tube C at the aspirating position P31c, P32c. Or in order to skip the supply of the washing fluid to the measurement unit, the piercing pipette 31d, 32d may be controlled not to aspirate the washing fluid in the washing fluid tube C.

Figure 14:
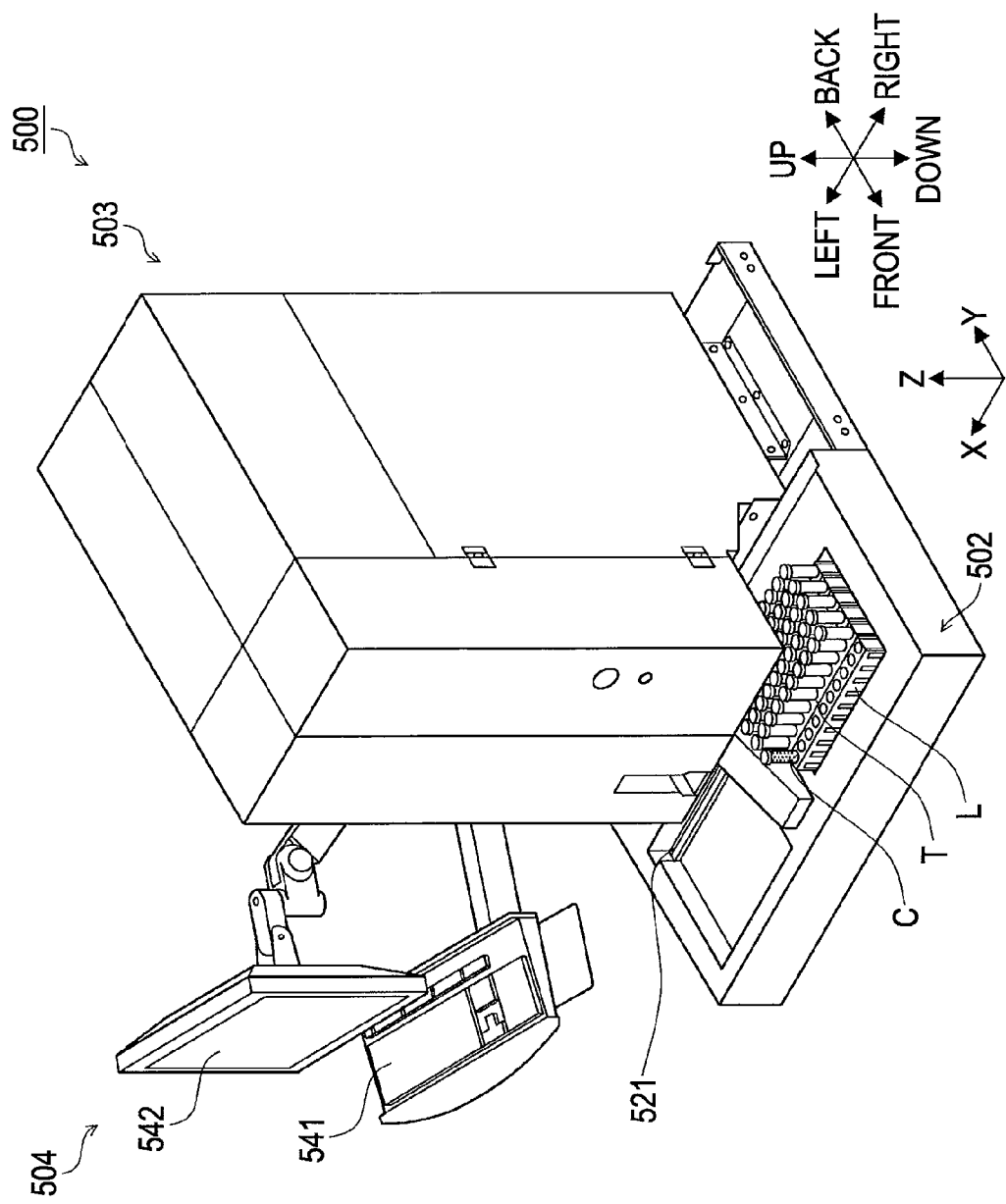
FIG. 14 is a view showing an outer appearance of a sample analyzer according to modified embodiment 1.

The sample analyzer 1 including two measurement units 31, 32 has been illustrated in the above described embodiment, but three or more measurement units may be arranged and a smear creating device may be arranged other than the measurement unit. A sample analyzer 500 including one measurement unit 503 may be provided as shown in modified embodiment 1 of FIG. 14. In this case, the transportation unit 502 has a rack transporting portion 521 configured shorter than in the embodiment described above, but an information processing unit 504 and other configurations are configured similar to the above.

Figure 15B:
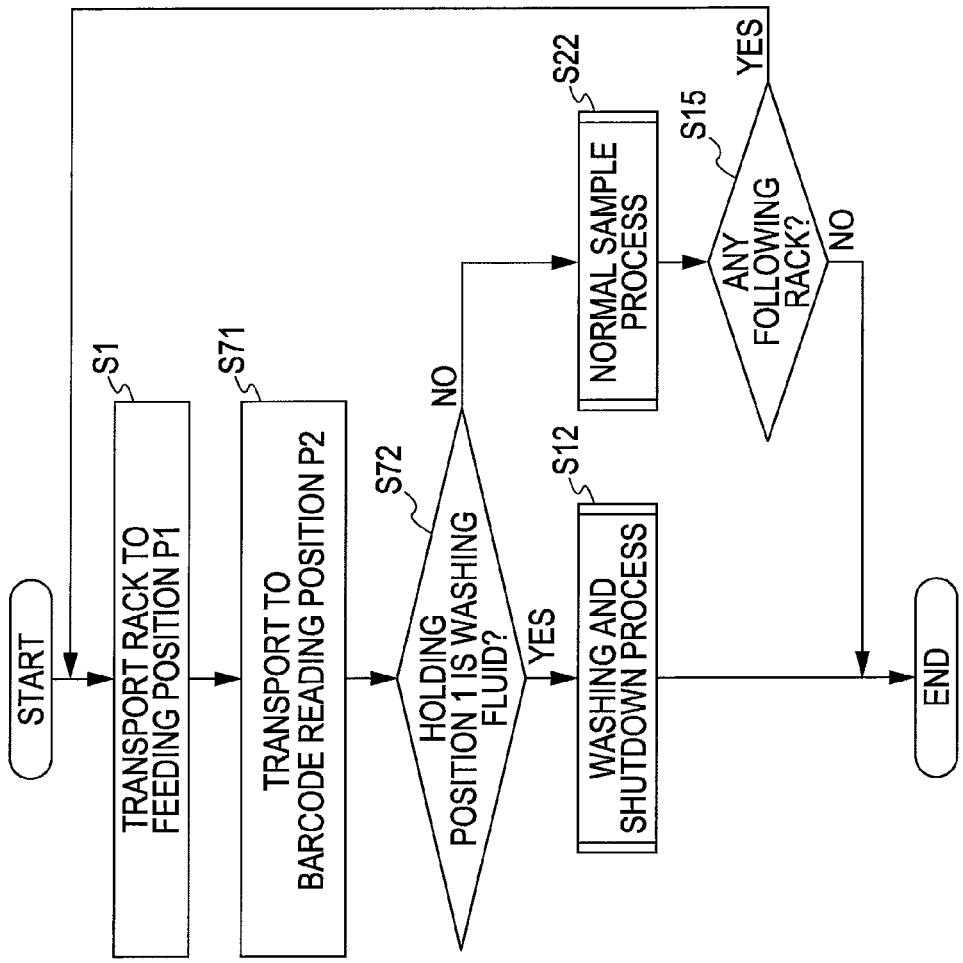
FIG. 15B is a view showing a flowchart of operation of rack according to modified embodiment 1.
Figure 15A:
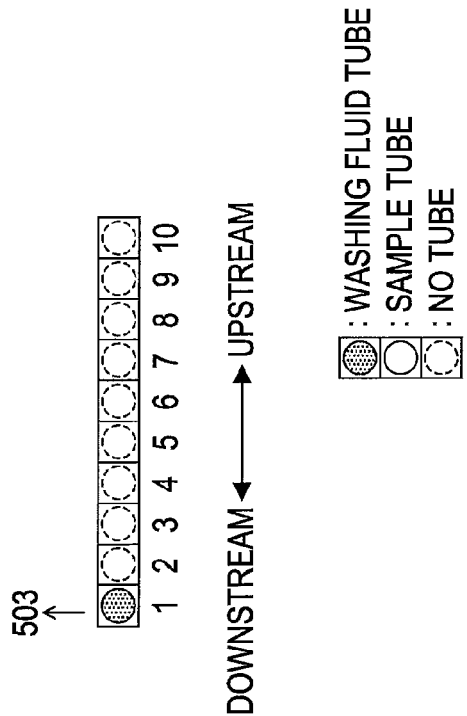
FIG. 15A is a view showing an arrangement rule of the washing fluid tubes according to modified embodiment 1.

FIG. 15A is a view showing an arrangement rule of the rack L of the washing fluid tube C used for the modified embodiment 1. The washing fluid tube C is installed at the holding position 1 which is the most downstream side position in the transporting direction.

FIG. 15B is a view showing a flowchart of the control operation of the rack L used for the modified embodiment 1. The processes similar to the embodiment described above shown in FIG. 9 are denoted with similar reference numerals, and the detailed description will be omitted.

In the modified embodiment 1, whether to perform the washing and shutdown process or perform the sample process is determined according to the type of tube arranged at the holding position 1.

When the rack L is transported to the feeding position P1 (S1), the CPU 401 operates the rack transporting portion 23 to transport the rack L so that the holding position 1 of the rack L is positioned at the barcode reading position P2 (S71). The barcode information of the tube installed at the holding position 1 is then read by the barcode unit B2, and the CPU 401 determines whether the washing fluid tube C is at the holding position 1 (S72). If the washing fluid tube C is at the holding position 1 (S72:YES), determination is made that the holding position 1 is in conformity with the normal arrangement rule of the washing fluid tube C shown in FIG. 15A. In this case, the washing and shutdown process is executed (S12). If the washing fluid tube C is not at the holding position 1 (S72: NO), it is determined that the arrangement of the tubes is not adapted to perform a washing. The CPU 401 executes the normal sample process (S22). The following holding position determination steps S102 to S108 (see FIG. 11) in the washing and shutdown process S12 and the following holding position determination steps S201 to S205 (see FIG. 12) in the normal sample process S22 are then modified to include the holding position 2 so that the holding positions 2 to 10 are the target of determination, but the illustration will be omitted herein.

In modified embodiment 1, therefore, effects similar to the embodiment described above are obtained even with the configuration including one measurement unit.

In the embodiment described above, if the sample tube T is held on the upstream of the washing fluid tube C, the supply of the washing fluid tube C and the sample tube T to the measurement units 31, 32 is skipped and the rack L is transported to the collecting position P4, but only the washing fluid tube C may be skipped and the sample tube T arranged on the upstream may be supplied to the measurement units 31, 32 to execute the measurement process, as shown in modified embodiment 2 of FIG. 16.

FIG. 16A is a view in which one part of FIG. 9 is changed, and FIG. 16B is a view in which one part of FIG. 11 is changed.

With reference to FIG. 16A, in the case of modified embodiment 2, the CPU 401 displays a sample detection warning message Er3 shown in FIG. 16C (S81) if the holding position 2 is the sample tube T (S11:YES). A message telling that the analyzer will skip the process of the washing fluid tube C and prioritize the measurement of the sample is displayed in the help dialogue D1. When the confirm button D15 of the help dialogue D1 is pushed, the CPU 401 skips the process of the detected washing fluid tube C at the holding position 1 (S82). The CPU 401 executes the normal sample process (S22).

With reference to FIG. 16B, in the case of modified embodiment 2, if the sample tube T is set at the holding positions 3 to 10 (S104: NO), the sample detection warning message Er3 is displayed as shown in FIG. 16C (S181). A message telling that the analyzer will skip the process of the washing fluid tube C and prioritize the measurement of the sample is displayed in the help dialogue D1. When the confirm button D15 of the help dialogue D1 is pushed, the process of the detected washing fluid tube C at the holding position 1 is skipped (S182). In this case, the CPU 401 executes the normal sample process (S201).

In the modified embodiment 2, the process of the following sample tube T is automatically started when the confirm button D15 is pushed after the washing fluid tube C is skipped, and thus the trouble of the user to again set the rack L in which only the sample tube T is installed in the right table 21 is alleviated.

In the embodiment described above and modified embodiment 2, the washing fluid tube C is automatically discharged to the left table 22 without being supplied to the measurement units 31, 32 when the process for the washing fluid tube C is skipped. However it may be configured so that the process of the sample tube T is carried out, and thereafter, the washing fluid tube C may be supplied to the measurement units 31, 32. This configuration will be described as a modified embodiment 3 shown in FIG. 17. This mode can be realized by first supplying the sample tube T to the measurement unit 31, 32 and then lastly supplying the washing fluid tube C to the measurement unit 31, 32. Furthermore, in such a case where a washing fluid tube C is held in the preceding rack L and a sample tube T is held in the following rack L, it can be realized in the following manner. The preceding rack L may wait in the transportation space 231, and the sample tube T of the following rack L may be supplied to the measurement units 31, 32. After the supply of all the sample tubes T of the following rack L is finished, the following rack L is first discharged to the left table 22, and lastly, the preceding rack L is supplied to the measurement units 31, 32.

Figure 17:
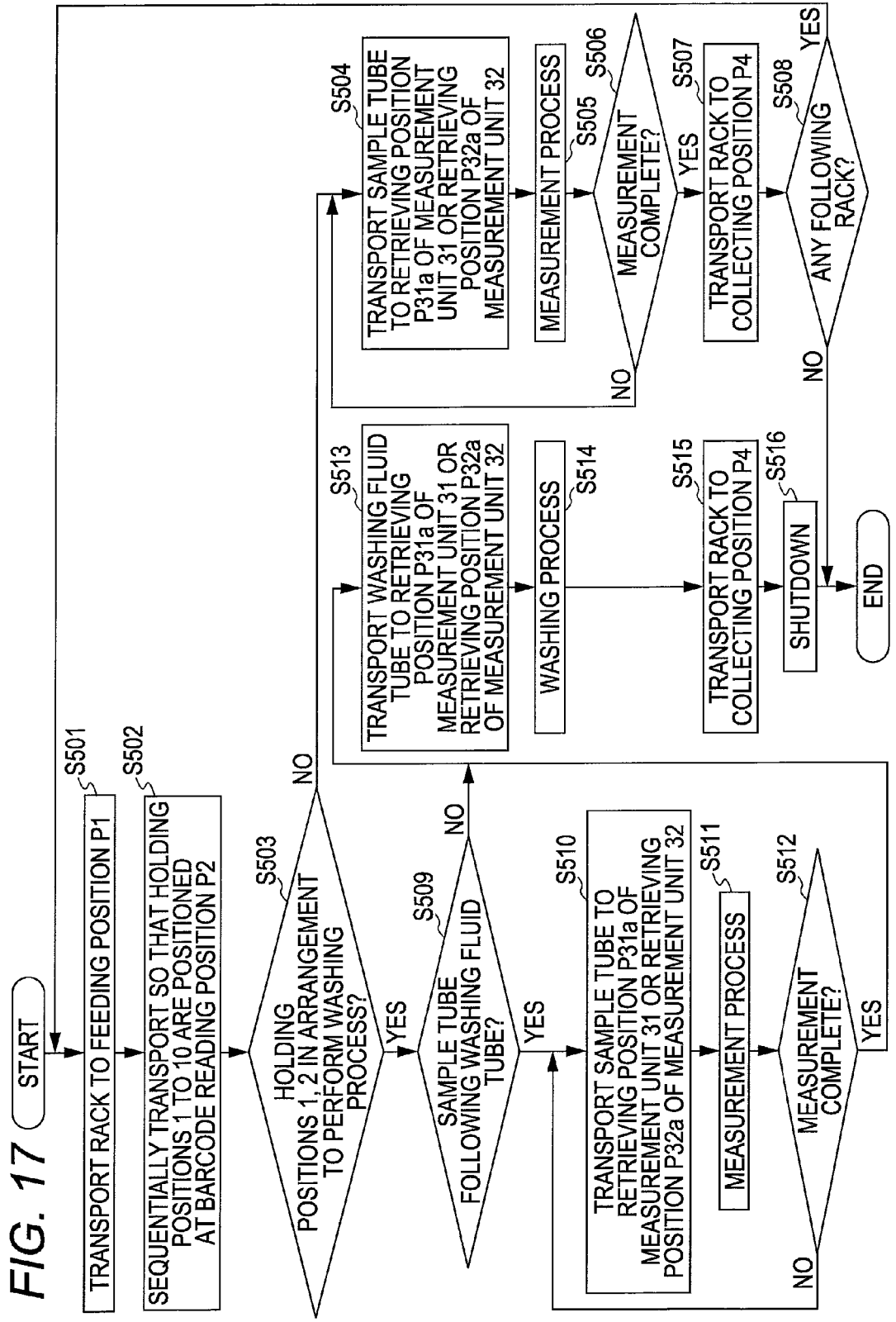
FIG. 17 is a view showing a flowchart of operation of rack according to modified embodiment 3.

FIG. 17 is a view showing a flowchart of control operation of the rack L when the washing fluid tube C and the sample tube T coexist in one rack L. In FIG. 17, the display process of the warning message is omitted, but the warning message may be displayed on the display section 42 in a similar manner with the embodiment described above if the arrangement of the tubes in the rack L is not in conformity with the normal arrangement rule.

First, the CPU 401 operates the rack transporting portion 23 to transport the rack L to the feeding position P1 (S501) and then to the barcode reading position P2 (S502) so that the holding positions 1 to 10 of the rack L are sequentially positioned at the barcode reading position P2. The CPU 401 then determines whether or not the tube arranged at the holding positions 1, 2 is in the arrangement to perform the washing process based on the read barcode information (S503). Specifically, the determination processes of S3, S4, and S21 of FIG. 9 are carried out.

If the tube arranged at the holding positions 1, 2 is not in the arrangement to perform the washing process (S503: NO), that is, the tube arranged at the holding positions 1 or 2 is a sample tube T, the CPU 401 operates the measurement unit 31, 32 to perform the measurement process of the sample tube T similar to the embodiment described above (S504 to S506). After the measurement process is completed (S506: YES), the CPU 401 operates the rack transporting portion 23 to transport the rack L to the collecting position P4 (S507) and performs the determination on the presence or absence of the following rack (S508). The CPU 401 returns the process to S501 if there is a following rack L (S508: YES), and completes the process for all racks L if there is no following rack L (S508: NO).

If the tube arranged at the holding positions 1 or 2 is in the arrangement to perform the washing process (S503: YES), the CPU 401 determines whether the sample tube T is arranged at the holding position following the washing fluid tube C (S509). The CPU 401 proceeds the process to S513 if the sample tube T does not follow the washing fluid tube C (S509: NO). If the sample tube T follows the washing fluid tube C (S509: YES), the CPU 401 operates the measurement unit to perform the measurement process of the sample tube T (S510 to S512) before performing the washing process of the washing fluid tube C.

If the measurement process is completed (S512: YES), the CPU 401 then performs the washing process of the measurement units 31, 32 using the washing fluid tube C arranged in the rack L (S513, S514).

When the washing process using the washing fluid tube C is completed after the measurement process of the sample tube T arranged in the rack L is completed, the CPU 401 operates the rack transporting portion 23 to transport the rack L to the collecting position P4 (S515) as described above. The CPU 401 then shuts down the measurement units 31, 32 and the information processing unit 4 (S516), and completes the process.

Therefore, according to the modified embodiment 3, the washing fluid tube C is once skipped and the measurement process of the sample tube T is performed, and thereafter the washing is executed using the washing fluid tube C. This may reduce the trouble of the user to rearrange the washing fluid tube C in the rack L and to again set the rack L in the right table 21.

In the embodiment described above and modified embodiment 2, when skipping the process of washing fluid tube C, the sample detection warning message Er1, Er3 is displayed, and the following processes are executed when the confirm button D15 is pushed, but the following processes may be executed without pushing the confirm button D15 and the display of warning message may be omitted.

If the user sufficiently understands the arrangement rule of the washing fluid tube C, such warning message may be omitted and the following processes may be automatically executed to smoothly perform the following processes.

In the embodiment described above, the sample tube T and the washing fluid tube C are installed in the rack L and supplied to the measurement unit 31, 32, however the embodiment is not limited to this mode. The rack transporting portion may be configured to receive a tube without using a rack and to transport the sample tube T or the washing fluid tube C to the measurement unit 31, 32 one at a time.

In the embodiment described above, the rack L includes a holder for ten tubes, but the number of holders may be other numbers. The arrangement rule of the washing fluid tube C is to be positioned on the most downstream in the transporting direction of the rack L but may be positioned at other positions. For instance, in the case of an arrangement rule where the washing fluid tube C should be arranged in the holding positions 5, 6, the supply of the washing fluid tube C to the measurement unit 31, 32 is skipped if the sample tube T is arranged at the holding positions 7 to 10 on the more upstream side.

Alternatively, the arrangement rule of the washing fluid tube C on the rack L may not be, and the washing operation may be automatically executed when the washing fluid tube C arrives. In this case as well, the supply of the washing fluid tube C to the measurement unit 31, 32 is skipped if the sample tube T follows the washing fluid tube C.

When the washing fluid tube C is held in the rack L according to the arrangement rule, whether the sample tube T is arranged in the following rack L is determined and the supply of the washing fluid tube C to the measurement unit 31, 32 may be skipped if the sample tube T is arranged. Accordingly, the processing of the sample that follows across the racks can be smoothly carried out even if the rule in which the washing fluid tube C is arranged at the most upstream holding positions 9, 10 is used.

Figure 18:
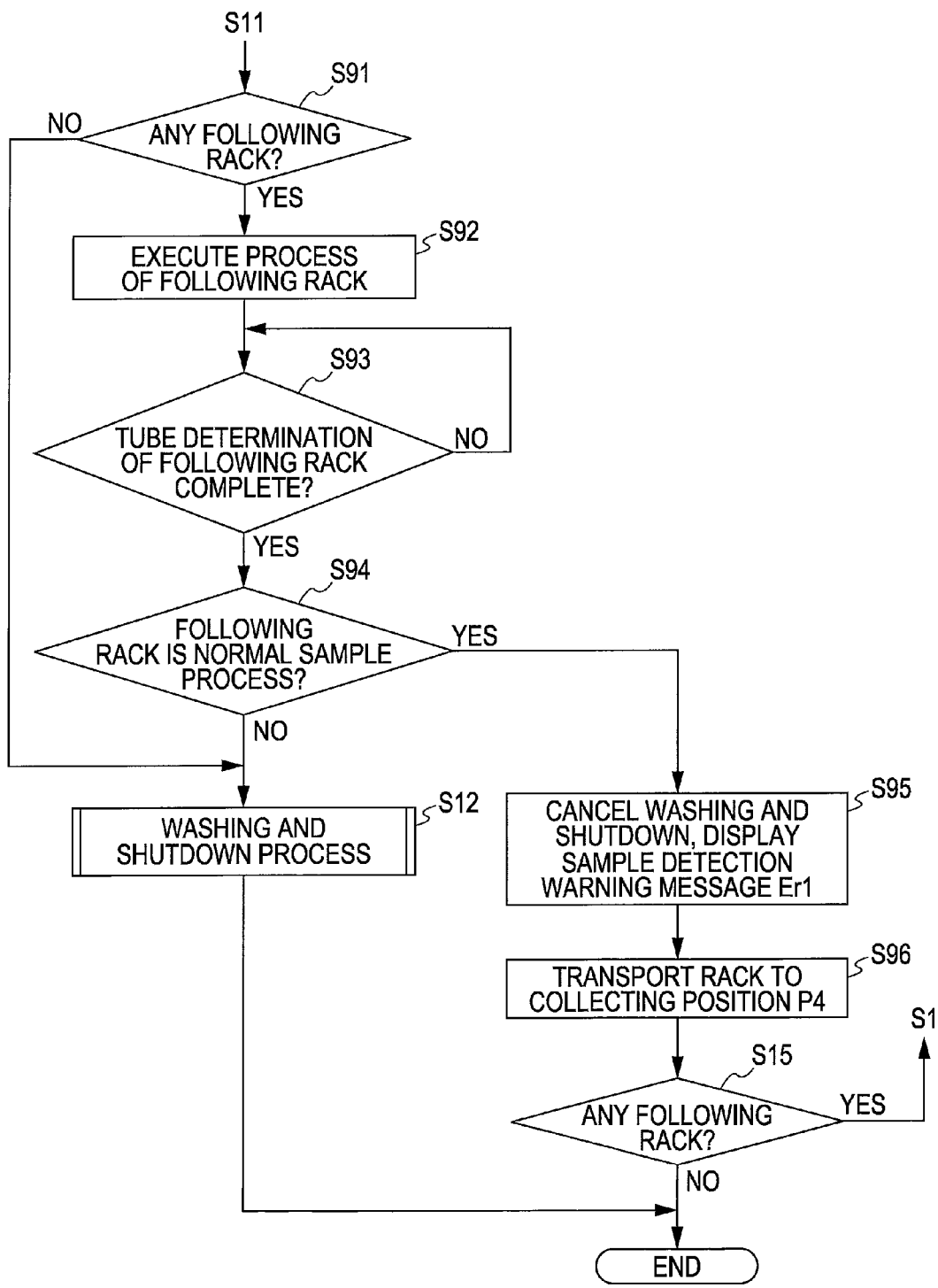
FIG. 18 is a view showing a flowchart of operation of rack according to modified embodiment 4.

FIG. 18 is a view showing a flowchart of the modified embodiment 4. This mode is adapted, in the case where a washing fluid tube C is arranged in the preceding rack L and a sample tube T is arranged in the following rack L, to skip the supply of the washing fluid and to supply the sample of the following rack L to the measurement unit 31, 32.

With reference to FIG. 18, in the modified embodiment 4, when determined that S11 shown in FIG. 9 is NO, the CPU 401 determines whether or not there is a following rack L (S91). If there is no following rack L (S91: NO), the process proceeds to S12, and the washing and shutdown process is carried out. If there is a following rack L (S91: YES), the CPU 401 proceeds the process of the following rack L (S92), and waits for the process on the preceding rack L until the determination of presence or absence of tube on the following rack L is completed (S93). After the determination on the following rack L is completed (S93: YES), whether or not the process on the following rack L is the normal sample process is determined (S94).

If the process on the following rack L is the normal sample process (S94: YES), the CPU 401 cancels the washing and shutdown process, and displays the sample detection warning message Er1 as shown in FIG. 10A (S95). When the confirm button D15 in the help dialogue D1 is pushed, the CPU 401 operates the rack transporting portion 23 to transport the rack L to the collecting position P4 (S96). The CPU 401 then determines whether there are any remaining rack in the right table 21 (S15), returns the process to S1 if there are racks L (S15: YES), and performs the process on the rack L. If there are not further following racks L (S15: NO), the process is completed.

If determined in S94 that the process on the following rack L is not the normal sample process (S94: NO), the process proceeds to S12, and the washing and shutdown process is carried out. In this case, the following rack L is discharged to the left table 22. The preceding rack L transported to the collecting position P4 is discharged to the left table 22 by the rack push-out mechanism 23a, whereby the process with respect to the preceding rack L is completed.

Therefore, according to the modified embodiment 4, when the sample tube T is held in a rack following a rack holding the washing fluid, the supply of the washing fluid tube C of the preceding rack L to the measurement unit 31, 32 is skipped. Thereby a washing is avoided from being automatically started. In this case, the process of the sample tube T of the following rack L is automatically started, so that the trouble of the user to again set the following rack L in the right table 21 can be alleviated.

In the flowchart of FIG. 18, the washing and shutdown process using a washing fluid tube C on the preceding rack L is canceled if the process on the following rack L is the normal sample process. However the analyzer may be configured, if the target of the washing and shutdown process by the washing fluid tube C on the preceding rack L is only one of the measurement units 31 and 32, to execute the washing and shutdown process only for the one of the measurement unit and to execute the normal sample process on the following rack L by the measurement unit, which is not the target of the washing and shutdown process.

In the embodiment described above, the presence or absence of the tube, and the type of sample tube T and washing fluid tube C are identified by the barcode unit B2, but may be identified with another identification means. For instance, an IC chip indicating the sample ID or the washing fluid ID may be arranged on the tube and an IC chip reader may be used to read the ID. Or an optical sensor for identifying the shape of tube may be used to identify the type of tube. A two-dimensional code arranged with dots such as the QR code (registered trademark) may be used in place of the linear barcode.

In the embodiment described above, the measurement units 31, 32 and the information processing unit 4 are automatically shut down after executing the washing of the measurement units 31, 32, however they may be restarted rather than being shut down. It is preferable that the user may set whether to perform the shutdown or perform the restart by use of the application program of the information processing unit 4.

In the embodiment described above, the analysis result is transmitted to the host computer 5, the necessity of the retest is determined by the host computer 5, and the necessity of the retest is acquired by the information processing unit 4, but the necessity of the retest may be determined by the information processing unit 4.

In the embodiment described above, the measurement units 31, 32 respectively perform the measurement of the sample and the process of the retest, but the measurement unit 32 on the upstream side may perform only an initial sample measurement, and the measurement unit 31 on the downstream side may perform only a retest.

The embodiment of the present invention may be appropriately modified within a scope of the technical idea described in the Claims.

What is claimed is:

1. A sample processing apparatus for processing a sample, the sample processing apparatus comprising:
   a sample processing section that aspirates samples in sample tubes and processes the aspirated samples;
   a transporting section that transports a plurality of tubes so that the sample processing section is sequentially supplied with the tubes;
   an identification section that acquires identification data of each tube being transported towards the sample processing section; and
   a system controller coupled to the sample processing section, the transporting section and the identification section and controlling operations of the sample processing section, the transporting section and the identification section, wherein the system controller is programmed to perform operations comprising:
   controlling the transporting section, upon acquisition of identification data of a washing fluid tube, to supply the washing fluid tube to the sample processing section; and
   controlling the sample processing section, when the washing fluid tube arrives at the sample processing section, to aspirate washing fluid in the supplied washing fluid tube and to perform washing of at least one part of the sample processing section,
   wherein
   the system controller is further programmed to control the sample processing section to:
   acquire identification data of a sample tube; and
   prohibit washing with aspirated washing fluid if the identification data of the sample tube is acquired after the identification data of the washing fluid tube is acquired and before washing is started.

2. The sample processing apparatus according to claim 1, wherein when the washing is prohibited, the system controller is also programmed to control the same processing section to prohibit processing of a sample from the sample tube which triggered the prohibition of washing.

3. The sample processing apparatus according to claim 1, wherein when washing is prohibited, the system controller is further programmed to control the sample processing section to aspirate a sample from the sample tube which triggered the prohibition of washing and to execute processing of the aspirated sample.

4. The sample processing apparatus according to claim 1, wherein when the washing is prohibited, the system controller is further programmed to control the sample processing section to aspirate and process a sample from the sample tube which triggered the prohibition of washing, and after processing of the sample is completed, the system controller is further programmed to then withdraw the prohibition of washing.

5. The sample processing apparatus according to claims 1, wherein the transporting section transports a rack capable of holding a group of the plurality of tubes.

6. The sample processing apparatus according to claim 5, wherein the identification section acquires identification data from the group of the plurality of tubes on the rack in an order from downstream in a transporting direction.

7. The sample processing apparatus according to claim 5, wherein the transporting section is capable of simultaneously transporting two racks on an identical transportation path; and
the identification section continuously acquires identification data from the group of tubes in each of the two racks.

8. The sample processing apparatus according to claim 1, further comprising an output section, wherein the system controller outputs a warning to the output section when washing is prohibited.

9. The sample processing apparatus according to claim 1, wherein the sample processing section automatically shuts down after performing washing.

10. The sample processing apparatus according to claim 1, wherein the sample processing apparatus is a sample analyzer that analyzes the sample.

11. A sample processing apparatus for processing a sample comprising:
a sample processing section that aspirates and processes samples in sample tubes;
a transporting section that transports a plurality of tubes in a rack, so that the sample processing section is sequentially supplied with the tubes, wherein a predetermined holding position in the rack is designated and assigned for a washing fluid tube;
an identification section that acquires identification data of each tube being transported towards the sample processing section; and
a system controller coupled to the sample processing section, the transporting section and the identification section and controlling operations of the sample processing section, the transporting section and the identification section,
wherein the system controller is programmed to perform operations comprising:
determining whether the predetermined holding position in the track is occupied by a washing fluid tube, or a sample tube based on identification data of a tube arranged in the holding position;
upon determination that the predetermined holing position is occupied by the sample tube, determining whether a washing fluid tube is arranged in a subsequent position to the predetermined holding position;
upon determination that no washing fluid tube is arranged in the subsequent position, controlling the sample processing section to perform a normal sample process for aspirating and processing a sample from the sample tube;
upon determination that the predetermined holing position is occupied by the washing fluid tube, determining whether a sample tube is arranged in a subsequent position to the predetermined holing position;
upon determination that no sample tube is arranged in the subsequent position, controlling the transporting section to supply the washing fluid tube to the sample processing section and controlling the sample processing section, upon arrival of the washing fluid tube at the sample processing section, to aspirate washing fluid in the washing fluid tube supplied by the transporting section and to perform washing of at least one part of the sample processing section, and
upon determination that a sample tube is arranged in the subsequent position to the predetermined holing position, controlling the sample processing section to prohibit washing with the washing fluid tube.

12. The sample processing apparatus according to claim 11, wherein when washing is prohibited, the system controller is further programmed to control the transporting section not to supply the sample tube to the sample processing section.

13. The sample processing apparatus according to claim 11, wherein when washing is prohibited, the system controller is further programmed to control the transporting section to transport the washing fluid tube without supplying to the sample processing section and to supply the sample tube to the sample processing section.

14. The sample processing apparatus according to claim 11, wherein when washing is prohibited, the system controller is programmed to control the transporting section to supply the sample tube to the sample processing section prior to the washing fluid tube, and then supply the washing fluid tube to the sample processing section after a normal sample process of a sample from the supplied sample tube is completed.

15. The sample processing apparatus according to claim 11, wherein the transporting section transports a rack for holding a group of the plurality of tubes.

16. The sample processing apparatus according to claim 15, wherein the identification section acquires identification data from the group of the plurality of tubes on the rack in an order from downstream in a transporting direction.

17. The sample processing apparatus according to claim 15, wherein the transporting section simultaneously transports two racks along an identical transportation path; and
the identification section continuously acquires the identification data from the group of the tubes in each of the two racks.

18. The sample processing apparatus according to claim 11, further comprising an output section,
wherein the system controller outputs a warning to the output section when washing is prohibited as a supply of the washing fluid tube to the sample processing section is prohibited.

19. The sample processing apparatus according to claim 11, wherein the system controller controls the sample processing section to automatically shut down after performing washing.

* * * * *